United States Patent
Gamache et al.

(10) Patent No.: US 8,469,057 B2
(45) Date of Patent: Jun. 25, 2013

(54) DIAPHRAGM-SEALED VALVE HAVING A LOCKING MECHANISM

(75) Inventors: Yves Gamache, Adstock (CA); André Fortier, Adstock (CA)

(73) Assignee: Mecanique Analytique Inc., Adstock, QC (CA)

( * ) Notice: Subject to any disclaimer, the term of this patent is extended or adjusted under 35 U.S.C. 154(b) by 229 days.

(21) Appl. No.: 13/132,918

(22) PCT Filed: Dec. 7, 2009

(86) PCT No.: PCT/CA2009/001783
§ 371 (c)(1),
(2), (4) Date: Jun. 4, 2011

(87) PCT Pub. No.: WO2010/063125
PCT Pub. Date: Jun. 10, 2010

(65) Prior Publication Data
US 2011/0233440 A1 Sep. 29, 2011

(30) Foreign Application Priority Data
Dec. 5, 2008 (WO) ............... PCT/CA2008/002138

(51) Int. Cl.
*F16K 11/07* (2006.01)
(52) U.S. Cl.
USPC .............. 137/625.48; 137/316; 137/627.5; 251/62
(58) Field of Classification Search
USPC ........... 137/316, 597, 625.48, 627.5; 251/62; 73/863.71
See application file for complete search history.

(56) References Cited

U.S. PATENT DOCUMENTS

| | | | |
|---|---|---|---|
| 3,085,440 A | 4/1963 | Guenther | |
| 3,111,849 A | 11/1963 | Broerman | |
| 3,139,755 A * | 7/1964 | Reinecke et al. | 73/863.71 |
| 3,140,615 A | 7/1964 | Broerman | |
| 3,198,018 A | 8/1965 | Broerman | |
| 3,376,894 A | 4/1968 | Broerman | |
| 3,387,496 A | 6/1968 | Broerman | |
| 3,417,605 A | 12/1968 | Hahn | |
| 3,439,542 A | 4/1969 | McCray | |
| 3,492,873 A | 2/1970 | Broerman et al. | |
| 3,545,491 A | 12/1970 | Broerman | |
| 3,633,426 A * | 1/1972 | Broerman | 251/62 |
| 4,112,766 A | 9/1978 | Ragains | |

(Continued)

*Primary Examiner* — John K Fristoe Jr.
*Assistant Examiner* — Reinaldo Sanchez-Medina
(74) *Attorney, Agent, or Firm* — Price Heneveld LLP

(57) ABSTRACT

A valve includes a valve cap, a valve body, a diaphragm, biasing means and a locking mechanism. The valve cap includes a plurality of process conduits and process ports. The valve body faces the valve cap and includes a plurality of plunger passages extending therein. The diaphragm is positioned between the valve cap and the valve body. The valve body includes a plunger assembly, a first support structure and a second support structure. The plunger assembly includes a plurality of plungers, each slidable between a closed position and an open position. In the closed position, the plunger deforms the diaphragm in order to block communication between two of the process ports. In the open position, the plunger is retracted away from the diaphragm. Each plunger is either a normally closed plunger or a normally open plunger. The normally closed plungers are mounted upon first support structure and the normally open plungers are mounted upon the second support structure. The locking mechanism is for engaging the first support structure and thereby physically restraining the normally closed plungers in the open position. A valve body assembly is also described.

19 Claims, 27 Drawing Sheets

U.S. PATENT DOCUMENTS

| | | | |
|---|---|---|---|
| 4,276,907 A * | 7/1981 | Broerman | 137/637.2 |
| 4,333,500 A | 6/1982 | Broerman | |
| 4,898,210 A * | 2/1990 | Nitta | 137/614.19 |
| 5,188,334 A * | 2/1993 | Yoshii et al. | 251/7 |
| 5,601,115 A | 2/1997 | Broerman | |
| 6,202,698 B1 * | 3/2001 | Stearns | 137/627.5 |
| 6,216,739 B1 | 4/2001 | Fukushima et al. | |
| 6,640,688 B1 | 11/2003 | Harper | |
| 6,896,239 B1 | 5/2005 | Brenes | |
| 6,907,897 B2 | 6/2005 | Maula et al. | |
| 7,931,043 B2 * | 4/2011 | Gamache et al. | 137/15.04 |
| 2006/0042686 A1 | 3/2006 | Gamache | |

* cited by examiner

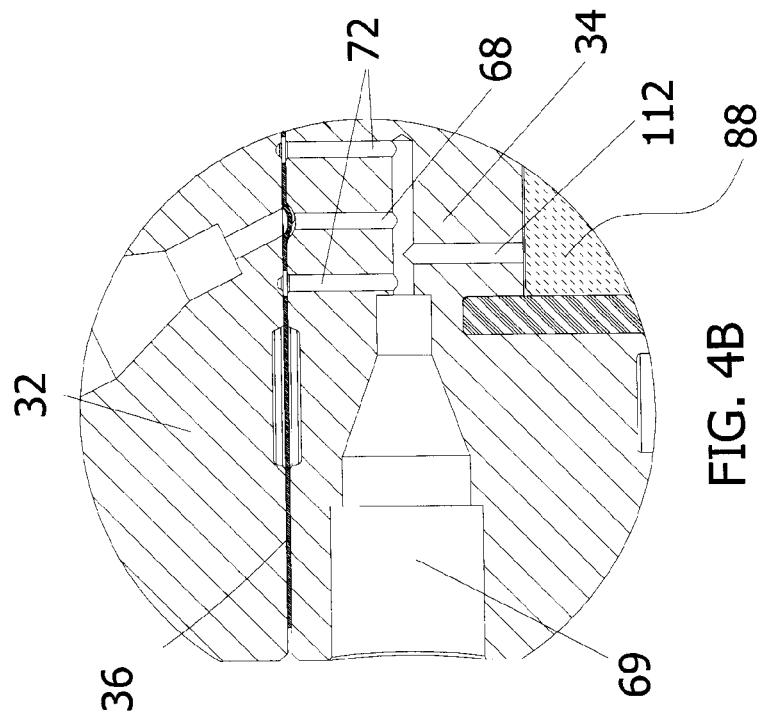
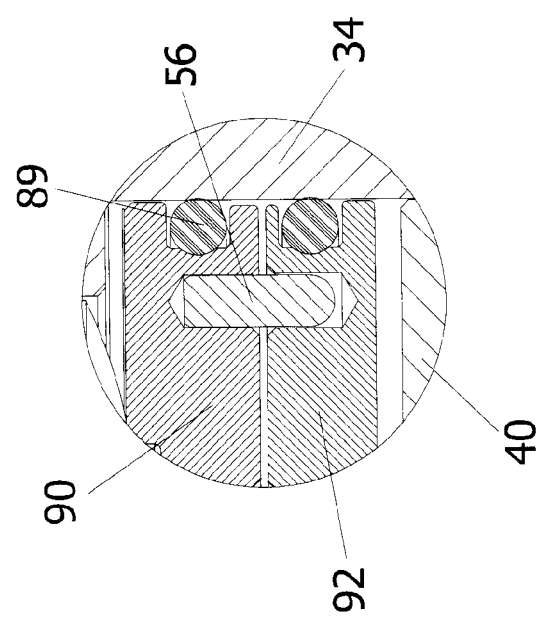
FIG. 4B
FIG. 4A

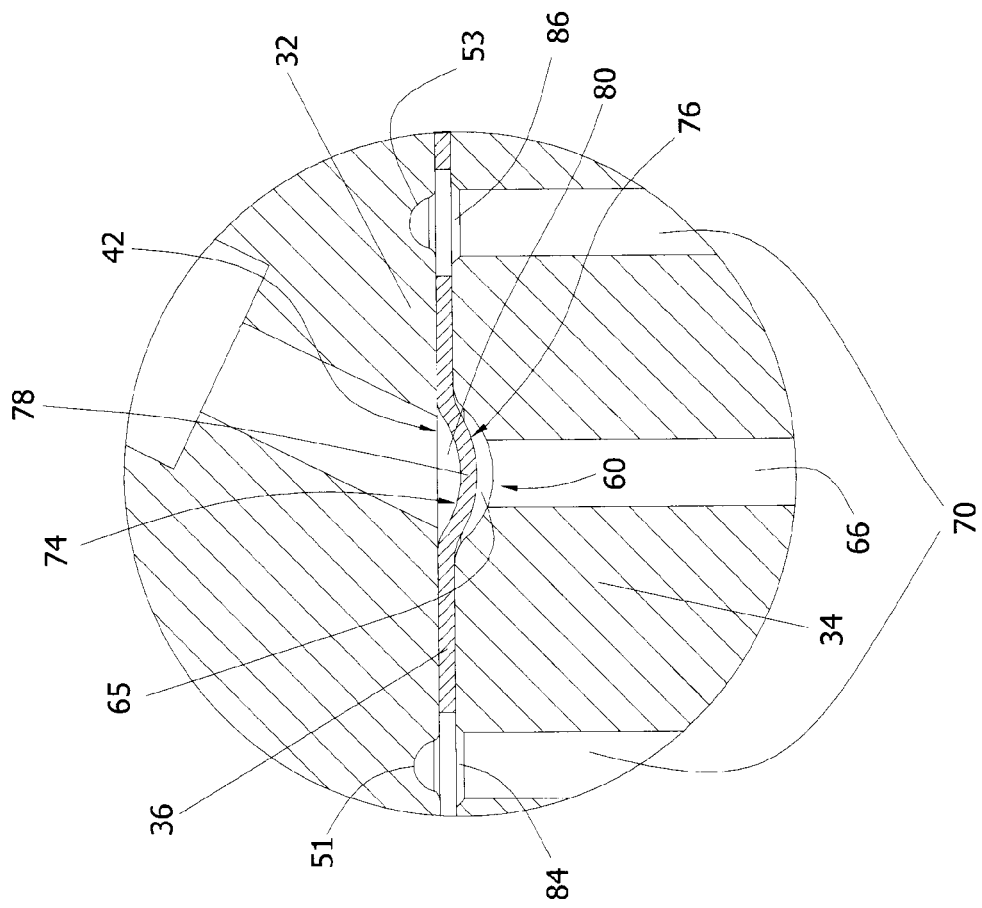
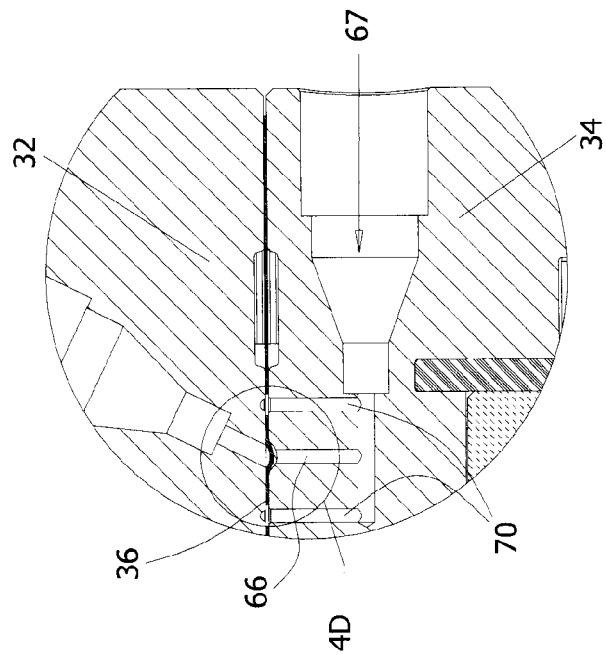
FIG. 4D
FIG. 4C

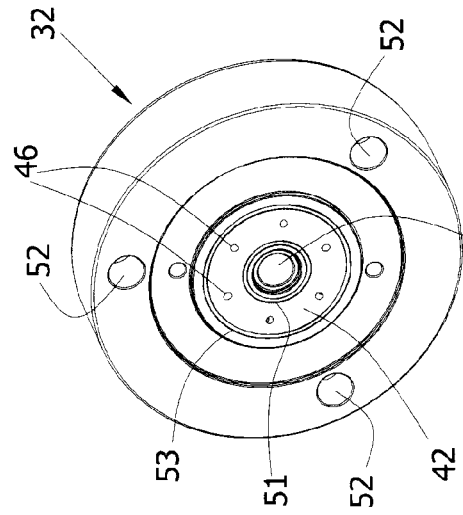
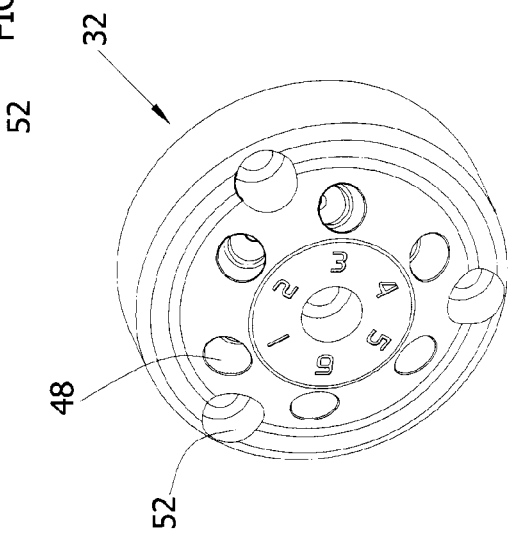
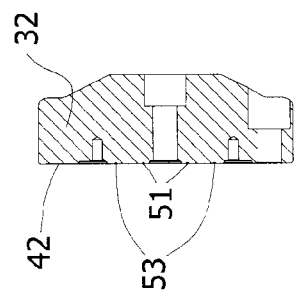
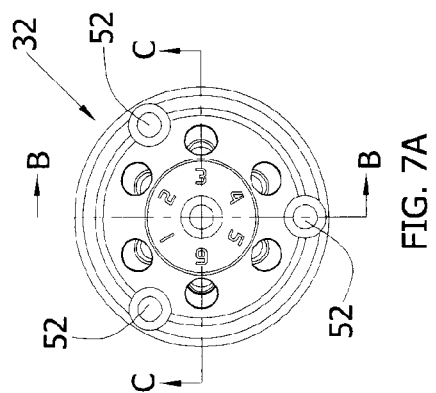
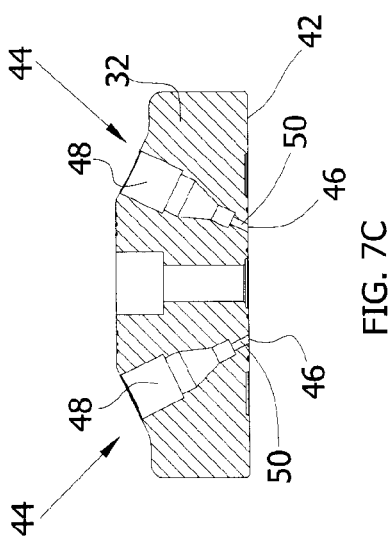

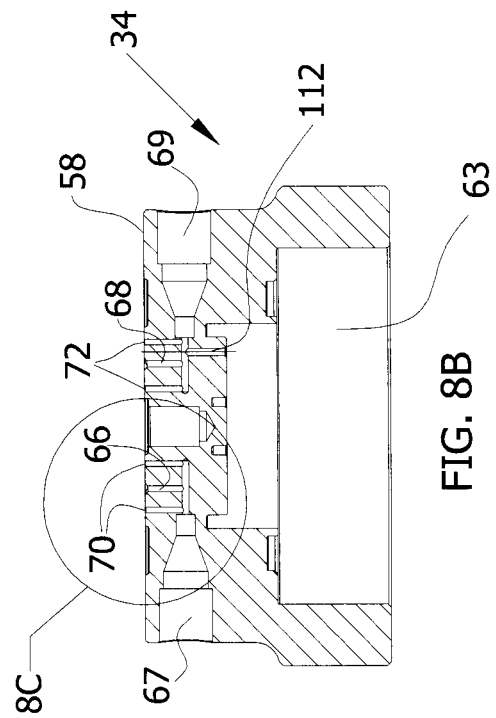
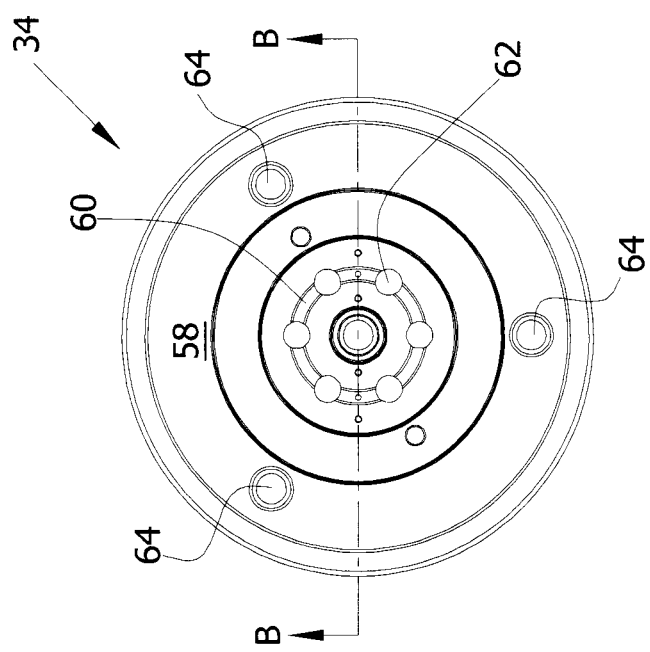
FIG. 8B
FIG. 8A

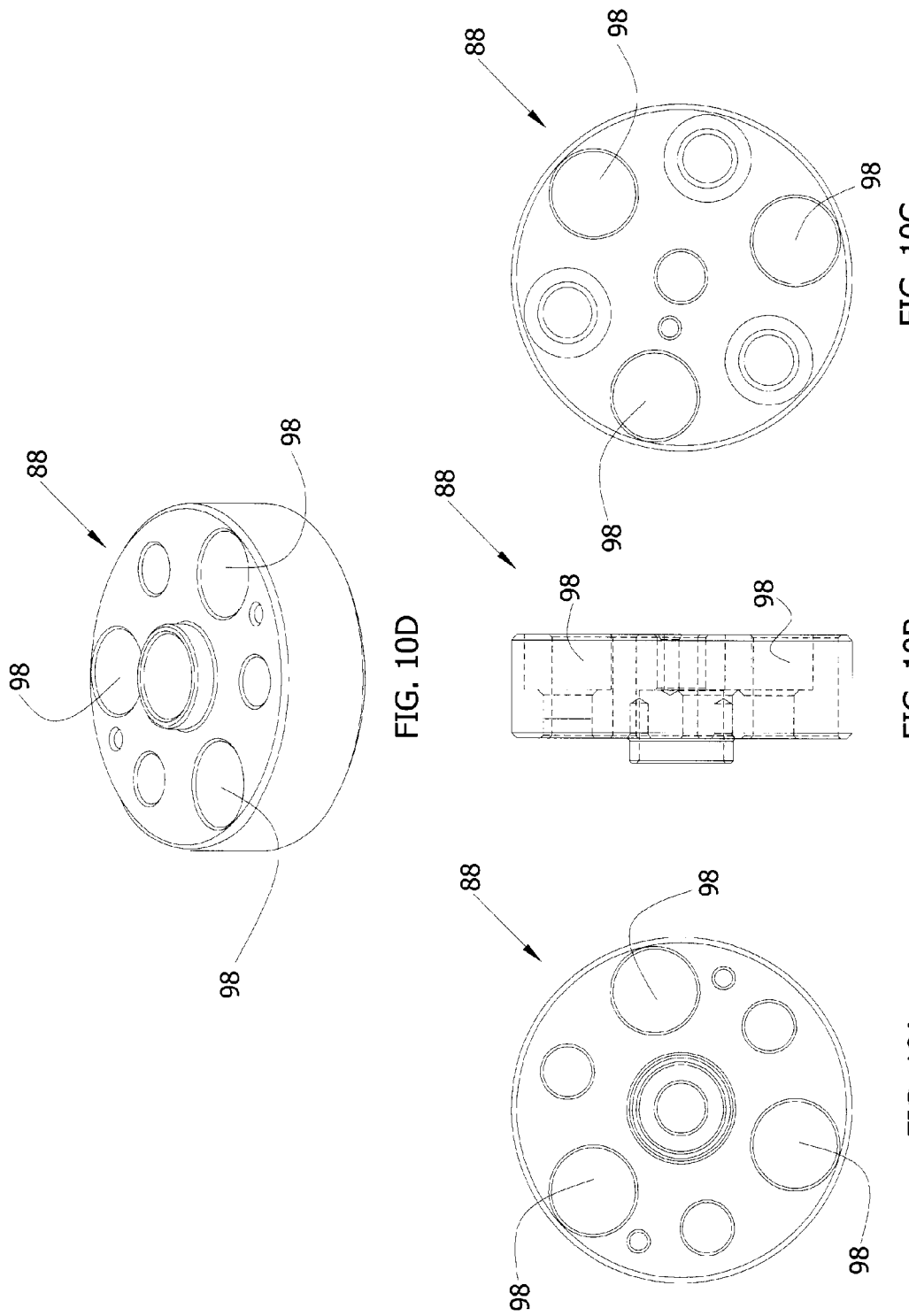

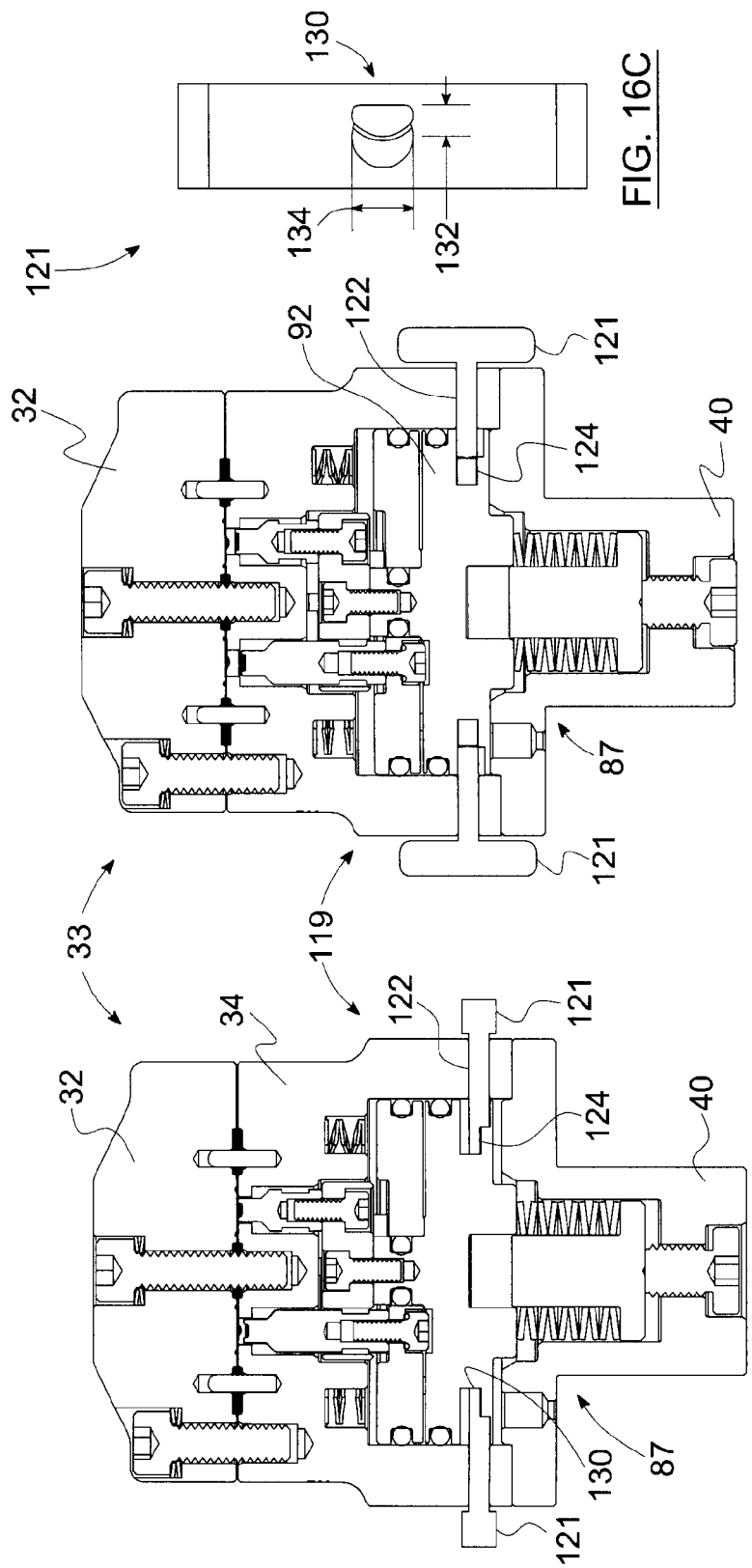

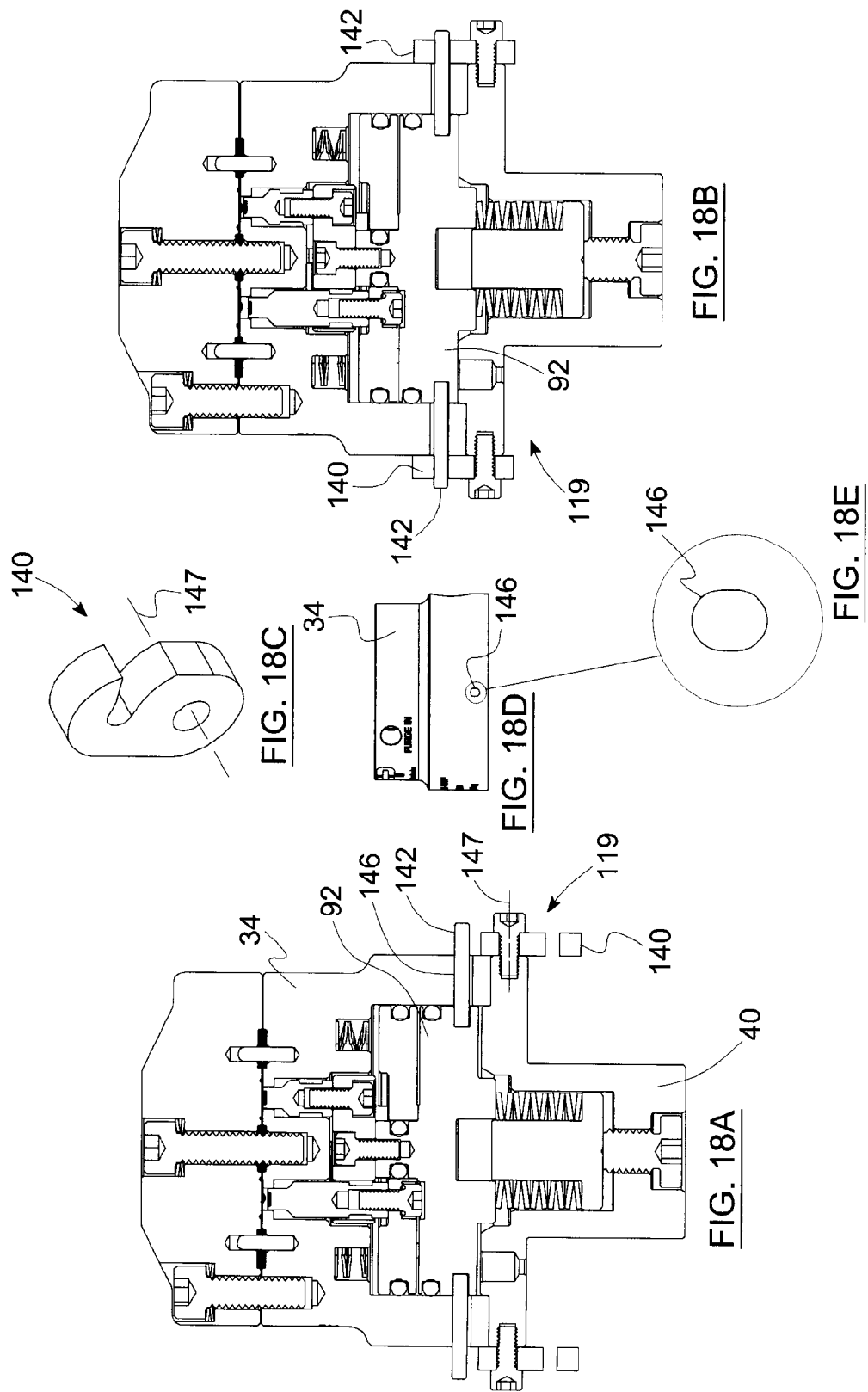

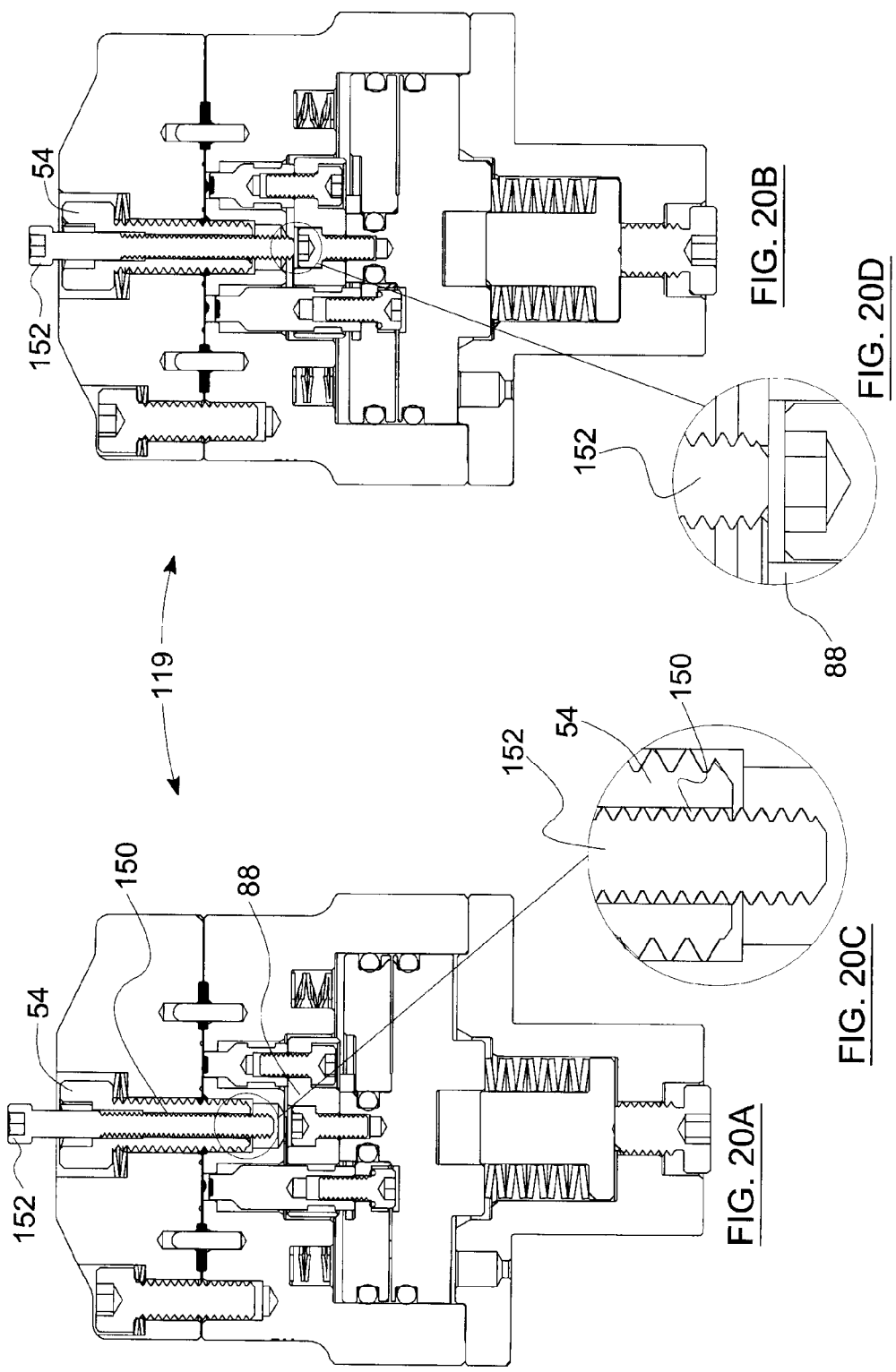

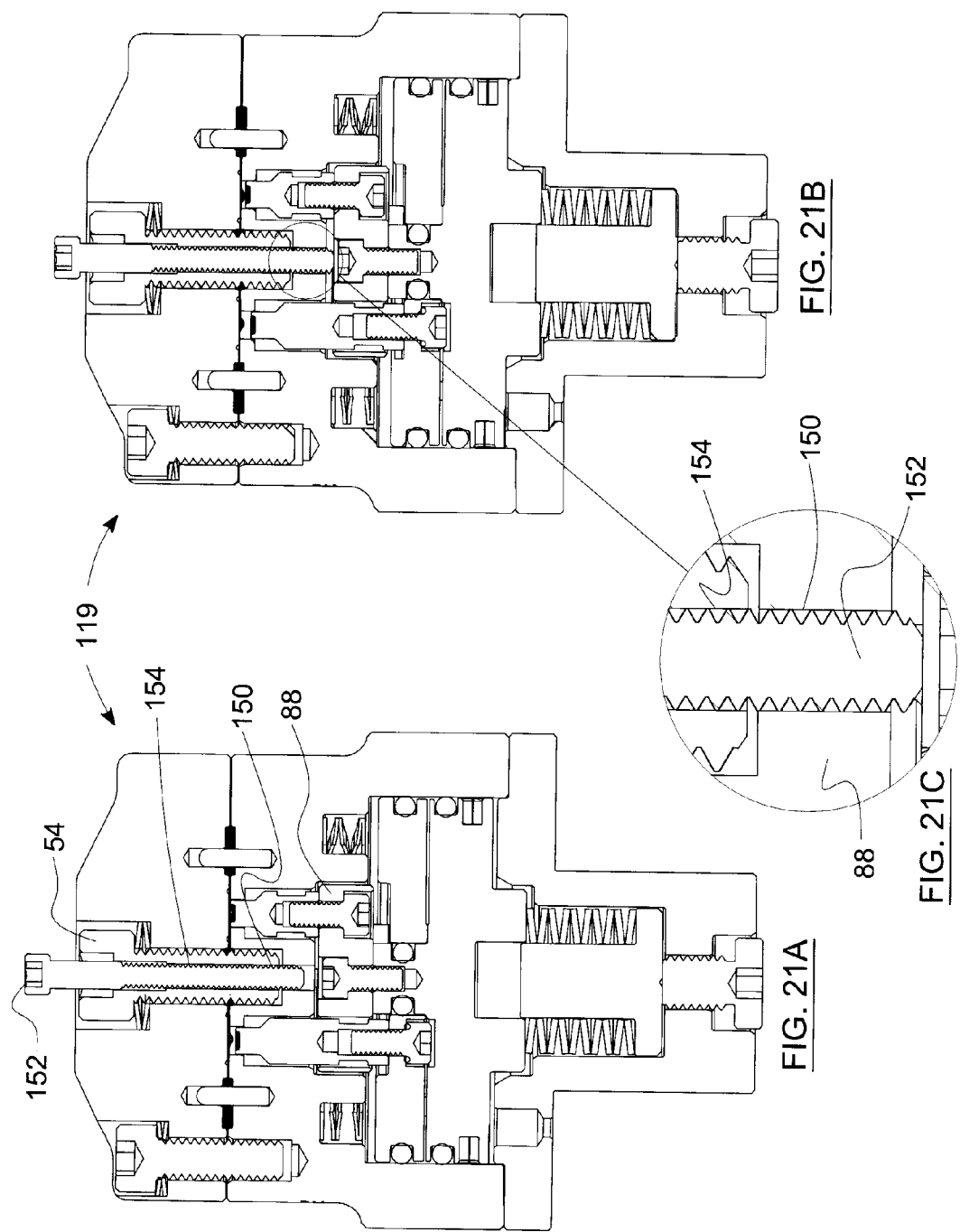

DIAPHRAGM-SEALED VALVE HAVING A LOCKING MECHANISM

FIELD OF THE INVENTION

The present invention generally relates to fluid analytical systems and more particularly concerns a valve and a valve body assembly having a locking mechanism.

BACKGROUND OF THE INVENTION

As well known by people involved in the art, chromatographic systems rely on the use of valves to allow reproducible sample introduction and various column switching schemes.

For the last forty years, many people have designed diaphragm valves for chromatography. Such diaphragm valves have been used in many commercially available gas chromatographs. They are apt to be integrated more easily in a gas chromatograph due to their physical size and since the actuator is embedded in the valve itself. These characteristics make them attractive for gas chromatograph manufacturers.

For example, international application no. PCT/CA2008/002138, filed Dec. 5, 2008 by the present applicants and published as WO2009/073966, discloses such a diaphragm-sealed valve. In addition, U.S. Pat. Nos. 7,216,528 and 7,503,203 issued to the present applicants May 15, 2007 and Mar. 17, 2009, respectively, discloses other types of diaphragm-sealed valves.

Referring now to FIG. 1 (PRIOR ART), there is shown an example of a typical diaphragm-sealed valve as known in the art. The valve 1 is provided with a top block 2 having an interface 4 and a plurality of ports 6. Each of the ports 6 opens at the interface 4 and has an inclined thread passage 8 to connect various analytical fitting and tubing (not shown). At the bottom of the inclined thread passage 8, there is a conduit 10 extending in the top block 2 and opening at the interface 4. The ports 6 are arranged on a circular line on the interface 4 of the top block 2. The interface 4 is advantageously flat and polished to minimize leaks between ports and from the ambient atmosphere. The valve 1 is also provided with a bottom block 12 and a diaphragm 14, which is generally made of polyimide, Teflon or other polymer material. The diaphragm 14 is positioned between the top block interface 4 and the bottom block 12, and has a recess 18 therein extending along the circular line formed by the ports 6 and biased away from the interface 4 of the top block 2. The recess 18 in the diaphragm 14 sits in a matching recess 20 made in the bottom block 12, thereby allowing some clearance for fluid circulation between adjacent ports 6.

The valve 1 is also provided with a plurality of plungers 16 mounted in the bottom block 12, each being respectively arranged to be able to compress the diaphragm 14 against the top block 2 at a position located between two of the ports 6. Preferably, as illustrated, when the valve is at rest, three plungers 16 are up while the other three are down. When the plungers are up, they compress the diaphragm 14 against the top block 2 and close the conduits made by the diaphragm recess 18, so that fluid circulation is blocked. The bottom block 12 keeps the plungers 16 and the actuating mechanism in position.

It is common to designate a portion of the plungers 16 as "normally open" and another portion as "normally closed". A normally open plunger 16 is biased downwards, i.e. away from the diaphragm 14, and therefore normally allows fluid circulation between the two adjacent ports 6. A normally closed plunger 16 is biased upwards, i.e. towards the diaphragm 14, and therefore blocks fluid circulation between the two adjacent ports 6. A user may actuate the valve 1 in order to alter the positions of the plungers 16, for example by sliding upwards and downwards the normally open and closed plungers 16, respectively.

However, it has been found that prolonged deformation of a diaphragm by a normally closed plunger, for example during storage or shipping, can damage the diaphragm. This damage can both shortens the diaphragm's life and compromise the system's performance. A damaged diaphragm can also increase the leak rate from port to port. When the pressure drop on the valve's ports differs from port to port, the pressure and flow may vary in the system. This causes detrimental effects on column performance and detector baseline.

There is therefore a need for an improved diaphragm-sealed valve.

SUMMARY OF THE INVENTION

In accordance with a first aspect of the present invention, there is provided a valve that includes a valve cap, a valve body, a diaphragm, biasing means and a locking mechanism. The valve cap includes a plurality of process conduits extending therethrough, each of the process conduits ending in a process port. The valve body faces the valve cap and includes a plurality of plunger passages extending therein. The diaphragm is positioned across the process ports and between the valve cap and the valve body. The valve body includes a plunger assembly, a first support structure and a second support structure. The plunger assembly includes a plurality of plungers. Each of the plungers is positioned in a respective one of the plunger passages and slideable therein between a closed position and an open position. In the closed position, the plunger deforms the diaphragm in order to block communication between two of the process ports. In the open position, the plunger is retracted away from the diaphragm. Each of the plungers is either a normally closed plunger or a normally open plunger. The normally closed plungers are mounted upon first support structure and the normally open plungers are mounted upon the second support structure. The biasing means are for biasing the normally closed plungers towards the diaphragm and biasing the normally open plungers away from the diaphragm. The locking mechanism is for engaging the first support structure and thereby physically restraining the normally closed plungers in the open position.

In accordance with a second aspect of the present invention, there is also provided a valve body assembly for a valve. The valve includes a valve cap that includes a plurality of process conduits extending therethrough. Each of the process conduits ends in a process port. The valve further includes a diaphragm positioned across the process ports. The valve body assembly includes a valve body, a plunger assembly, biasing means and a locking mechanism. The valve body includes a plurality of plunger passages extending therein. The diaphragm is positioned between the valve body and the valve cap. The plunger assembly includes a plurality of plungers, each of the plungers being positioned in a respective one of the plunger passages and slideable therein between a closed position and an open position. In the closed position, the plunger deforms the diaphragm in order to block communication between two of the process ports. In the open position, the plunger is retracted away from the diaphragm. Each of the plungers is either a normally closed plunger or a normally open plunger. The normally closed plungers are mounted upon first support structure and the normally open plungers are mounted upon the second support structure. The biasing means are for biasing the normally closed plungers towards the diaphragm and biasing the normally open plungers away from the diaphragm. The locking mechanism is for engaging the first support structure and thereby physically restraining the normally closed plungers in the open position.

Preferably, the locking mechanism includes a first transverse passage in the valve body which extends perpendicular to the plunger passages, a second transverse passage extending through the first support structure which is alignable with the first transverse passage when the normally closed plungers are in the open position, and a locking pin insertable through both the first and second transverse passages, thereby restraining the normally closed plungers in the open position.

Alternatively, the locking mechanism preferably includes an extension mounted to the first support structure and which extends through the valve body, the extension being movable with the first support structure as the normally closed plungers slide between the open and closed positions, and a restraining mechanism positionable between the valve body and the extension when the normally closed plungers are in the open position.

The locking mechanism may also alternatively include a threaded passage extending through the valve body parallel to the plunger passages, and a locking screw adapted to threadedly engage the threaded passage and be positioned at a locking position wherein the locking screw engages the first support structure thereby restraining the normally closed plungers in the open position.

It will be appreciated that a valve or valve body assembly in accordance with present invention may advantageously be used in a chromatographic system, or indeed in another application utilizing a diaphragm-sealed valve.

BRIEF DESCRIPTION OF THE DRAWINGS

These and other features and advantages of the invention will become apparent upon reading the detailed description and upon referring to the drawings in which:

FIGS. 4A, 4B and 4C are enlarged views of sections 4A, 4B, 4C of FIG. 4. FIG. 4D is an enlarged view of section 4D of FIG. 4C.

FIG. 7A is a top view of the valve cap of the valve of FIG. 2, according to a preferred embodiment of the present invention. FIG. 7B is a cross-sectional side view of the valve cap along line B-B of FIG. 7A. FIG. 7C is a cross-sectional view of the valve cap along the lines C-C of FIG. 7A. FIGS. 7D and 7E are a bottom perspective view and a top perspective view of the valve cap of FIG. 7, respectively.

FIG. 8A is a top view of the valve body of the valve of FIG. 2, according to a preferred embodiment of the present invention. FIG. 8B is a cross-sectional side view of the valve body along line B-B of FIG. 8A.

FIG. 10A is a top view of the push plate of the valve of FIG. 2, according to a preferred embodiment of the present invention. FIG. 10B is a side view of the push plate of FIG. 10A, FIG. 10C is a bottom view of the push plate of FIG. 10A while FIG. 10D is a top perspective view of the push plate of FIG. 10A.

FIG. 11A is a bottom perspective view of the normally open piston of the valve of FIG. 2, according to a preferred embodiment of the present invention, while

FIG. 12A is a bottom perspective view of the normally closed piston of the valve of FIG. 2, according to a preferred embodiment of the present invention, while

FIGS. 16A and 16B are cross-sectional views of a diaphragm-sealed valve according to a second preferred embodiment of the present invention. FIG. 16C is a front view a locking pin in accordance with the embodiment of FIGS. 16A and 16B.

FIGS. 18A and 18B are cross-sectional views of a diaphragm-sealed valve according to a fourth preferred embodiment of the present invention. FIG. 18C is a perspective view of a hook in accordance with the embodiment of FIGS. 18A and 18B. FIG. 18D is a side view of the cylinder of FIGS. 18A and 18B. FIG. 18E is an enlarged view of a portion of FIG. 18D FIGS. 19A and 19B are cross-sectional views of a diaphragm-sealed valve according to a fifth preferred embodiment of the present invention.

FIGS. 20A and 20B are cross-sectional views of a diaphragm-sealed valve according to a sixth preferred embodiment of the present invention. FIGS. 20C and 20D are enlarged views of portions of FIGS. 20A and 20B, respectively.

FIGS. 21A and 21B are cross-sectional views of a diaphragm-sealed valve according to a seventh preferred embodiment of the present invention. FIG. 21C is an enlarged view of a portion of FIG. 21B.

Figure 1:
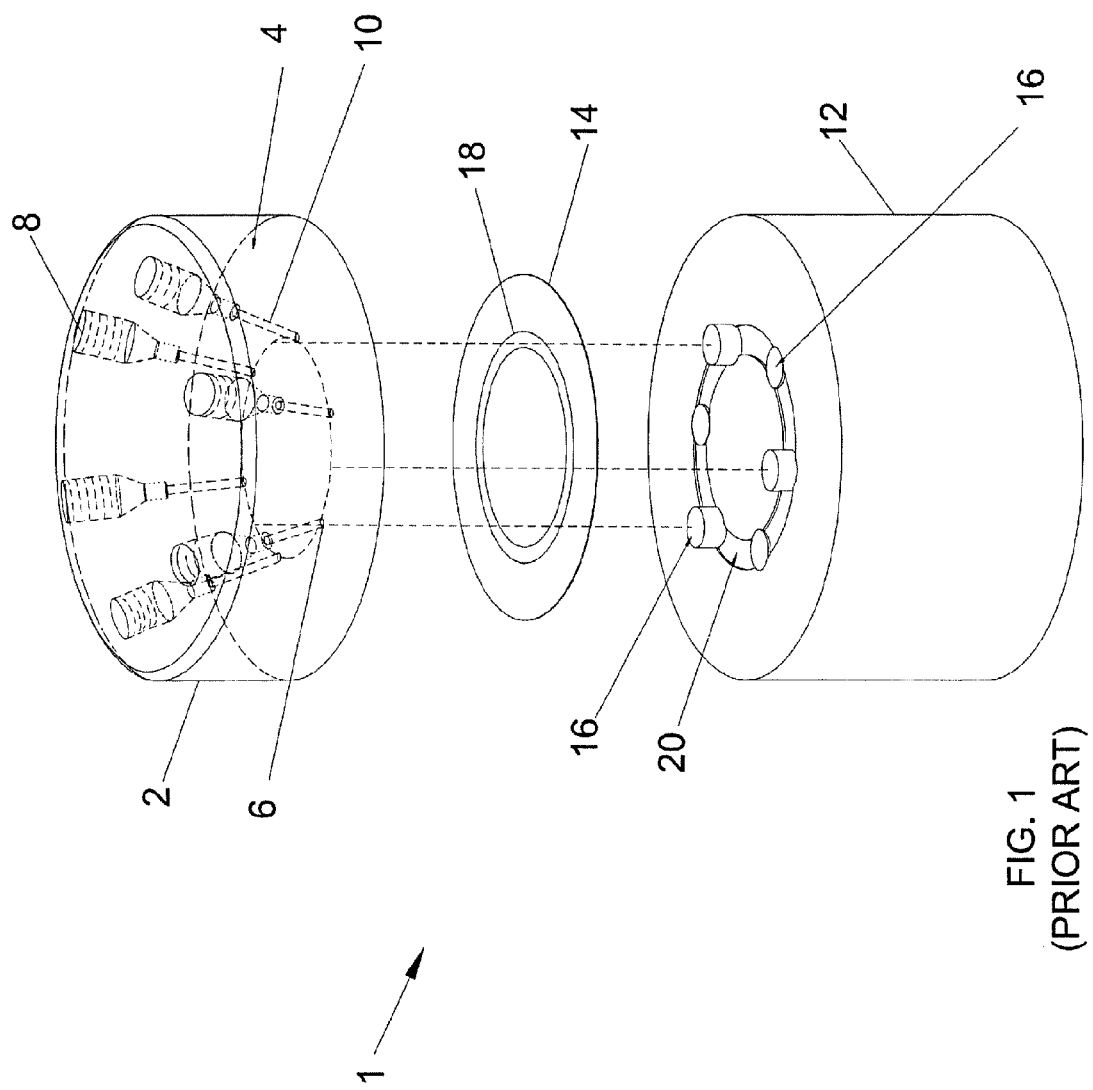
FIG. 1 (PRIOR ART) is an exploded perspective view of a diaphragm-sealed valve known in the art, in partial transparency.

While the invention will be described in conjunction with example embodiments, it will be understood that it is not intended to limit the scope of the invention to such embodiments. On the contrary, it is intended to cover all alternatives, modifications and equivalents as may be included as defined by the present application.

DESCRIPTION OF PREFERRED EMBODIMENTS

In the following description, similar features in the drawings have been given similar reference numerals. To preserve the clarity of the drawings, some references numerals have been omitted, if they were already identified in a preceding Figure.

Referring to FIGS. 2 and 4 to 6, there is shown a valve 30 according to a preferred embodiment of the present invention.

The valve 30 is of the diaphragm-sealed type valve. Such a valve may be used in analytical equipments of various types, and more particularly chromatographic equipments or online analyzers.

As illustrated in all of these Figures, the valve 30 includes four main elements: a valve cap 32, a valve body 33, a diaphragm 36 compressibly positioned between the valve cap 32 and the valve body 33, and a plunger assembly 38. The valve 30 may include a cylinder 34 and a bottom cap 40 or other equivalent structure holding the plunger assembly 38 to the valve body 33. In accordance with an aspect of the present invention, the valve 30 is also provided with a locking mechanism 119 which will be described in conjunction with FIGS. 14A to 21C below.

Valve Cap

Figure 4:
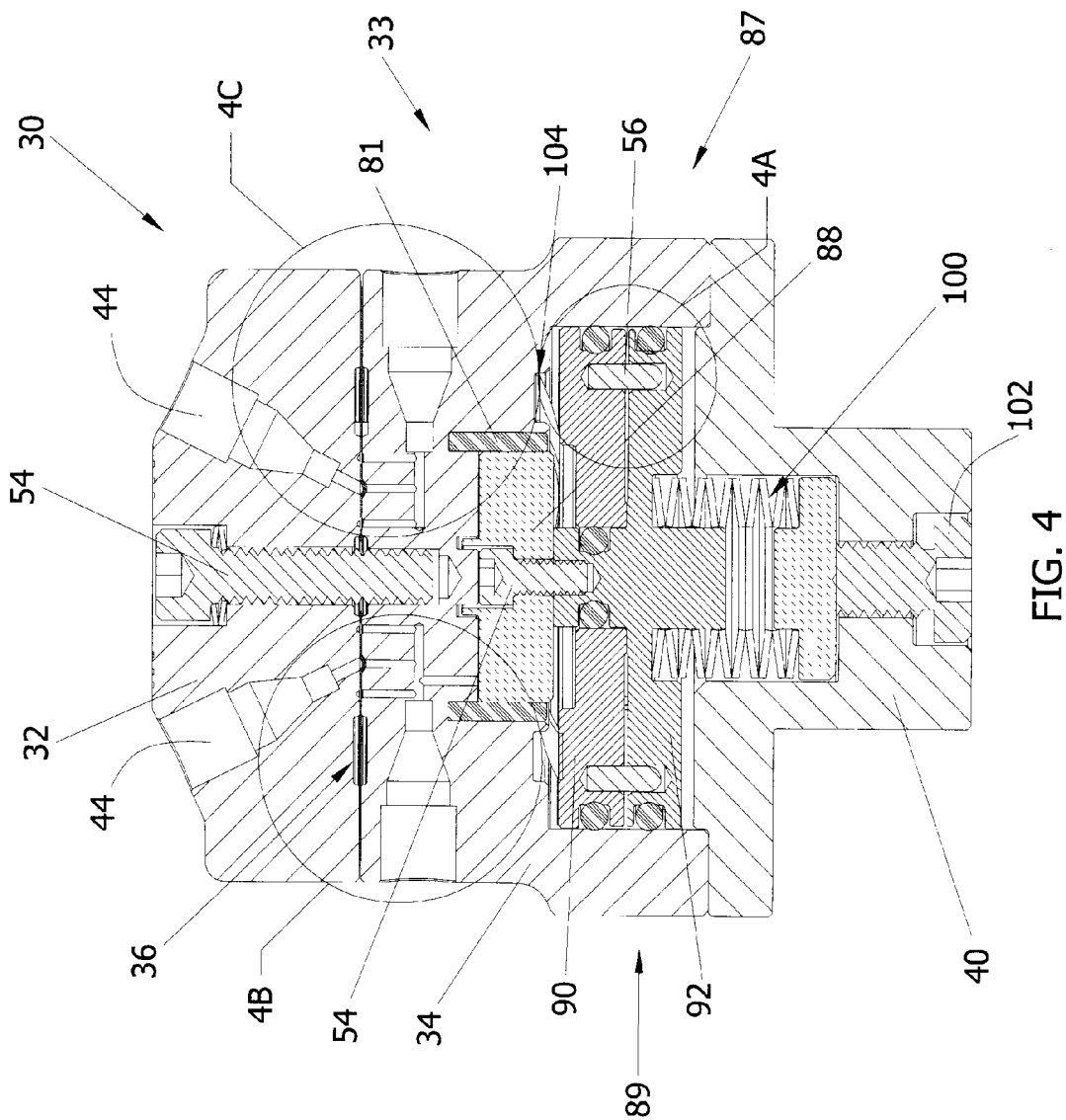
FIG. 4 is a cross-sectional side view of the diaphragm-sealed valve of FIG. 3 taken along line IV-IV.
Figure 5:
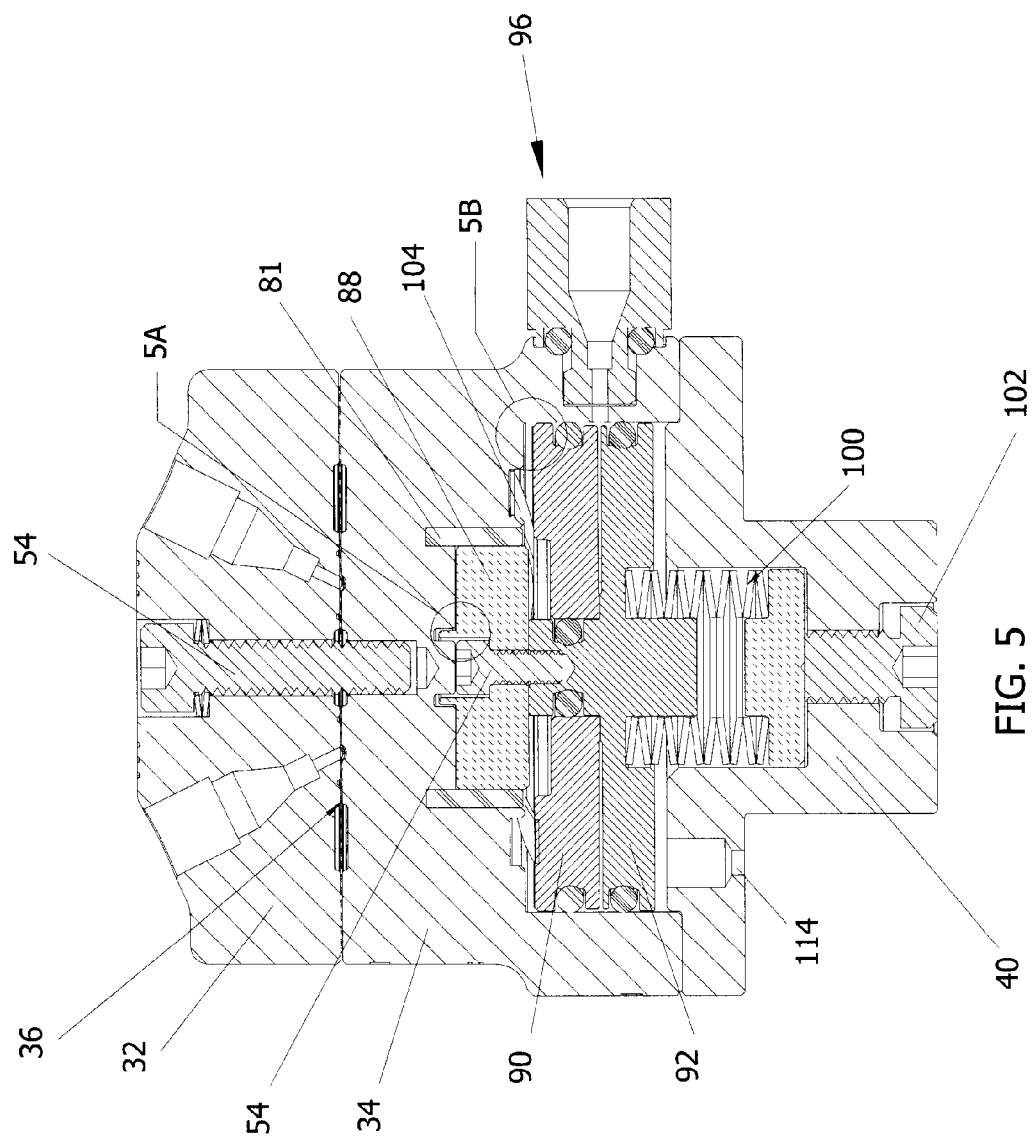
FIG. 5 is a cross-sectional side view of the diaphragm-sealed valve of FIG. 3 taken along line V-V.
Figure 5B:
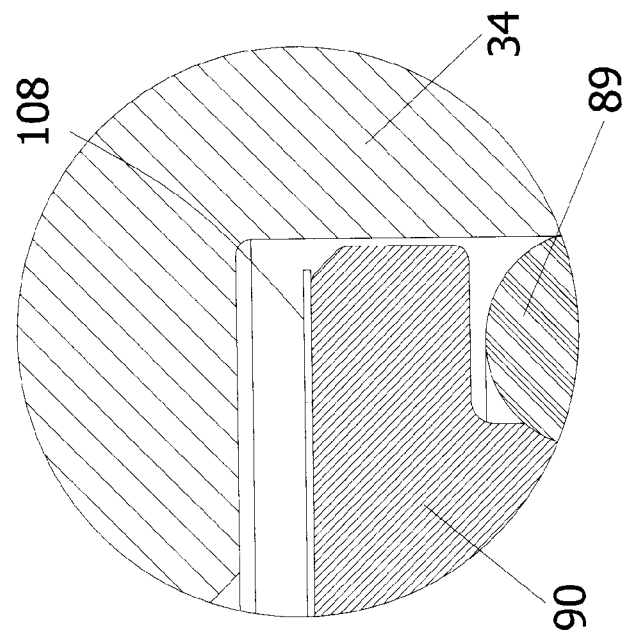
FIG. 5B is an enlarged view of section 5B of FIG. 5.
Figure 5A:
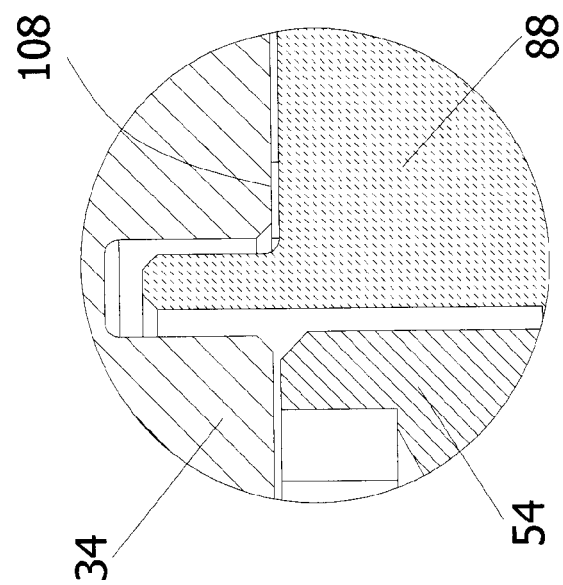
FIG. 5A is an enlarged view of section 5A of FIG. 5.
Figure 6:
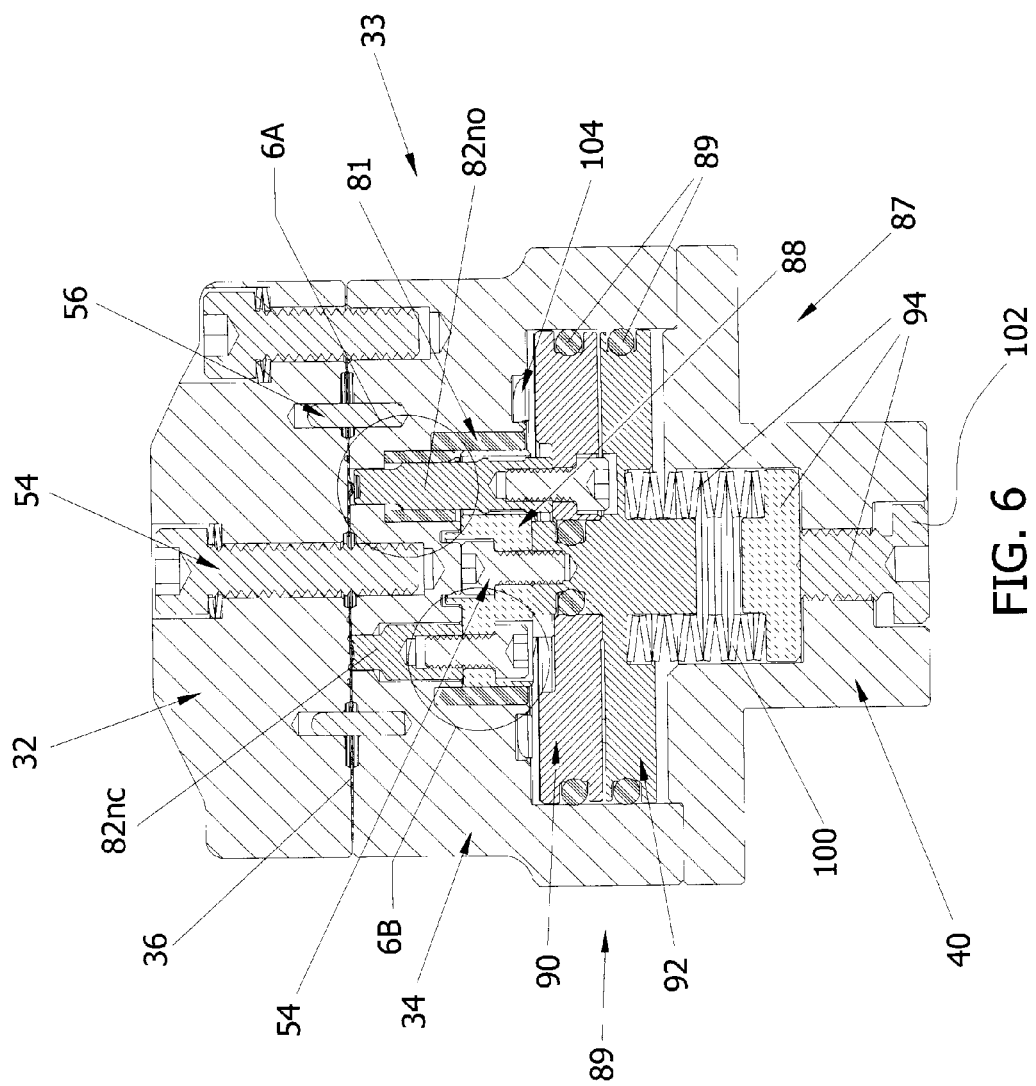
FIG. 6 is a cross-sectional side view of the diaphragm-sealed valve of FIG. 3 taken along line VI-VI.
Figure 6B:
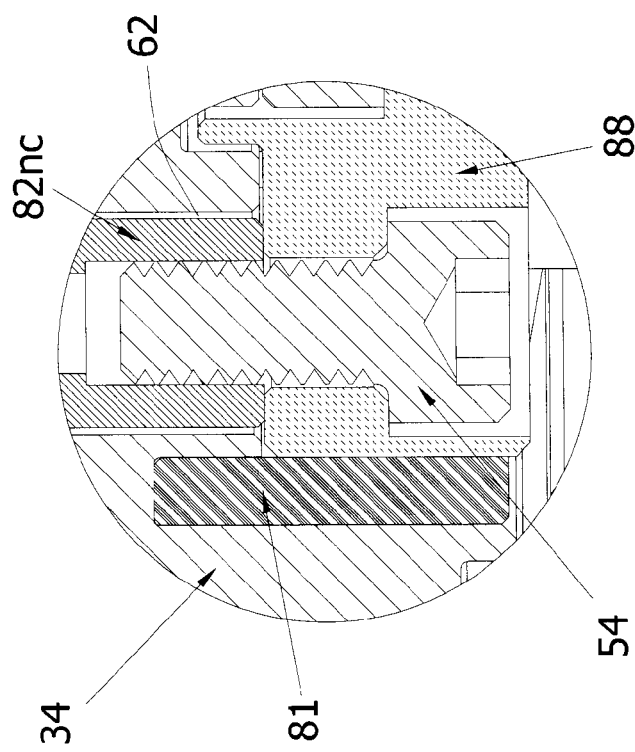
FIG. 6B is an enlarged view of section 6B of FIG. 6.
Figure 6A:
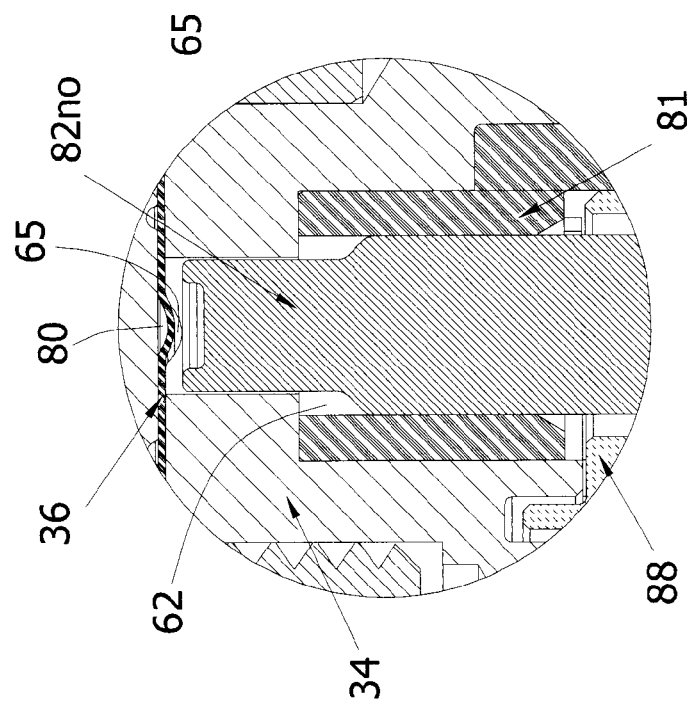
FIG. 6A is an enlarged view of section 6A of FIG. 6.
Figure 8D:
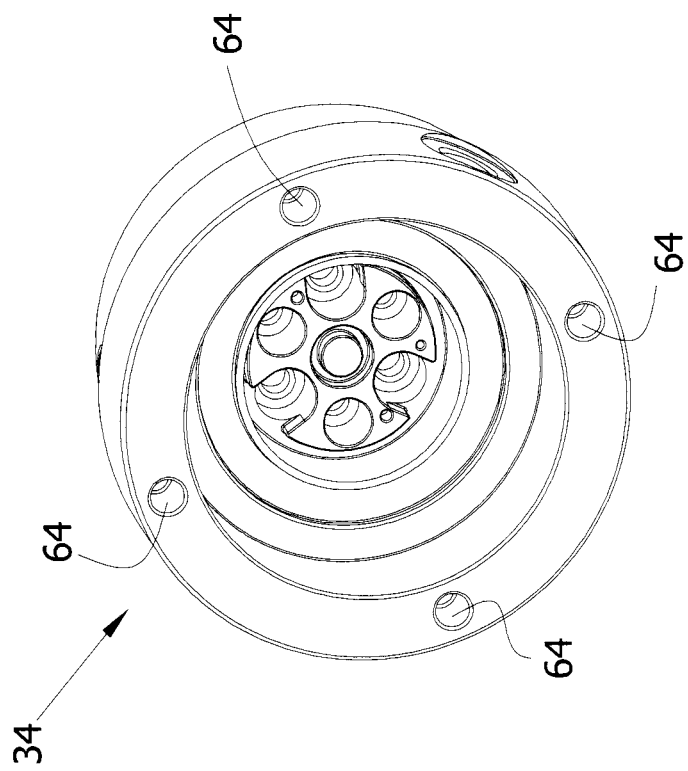
FIG. 8D is a bottom perspective view of the valve body of FIG. 8A.
Figure 8C:
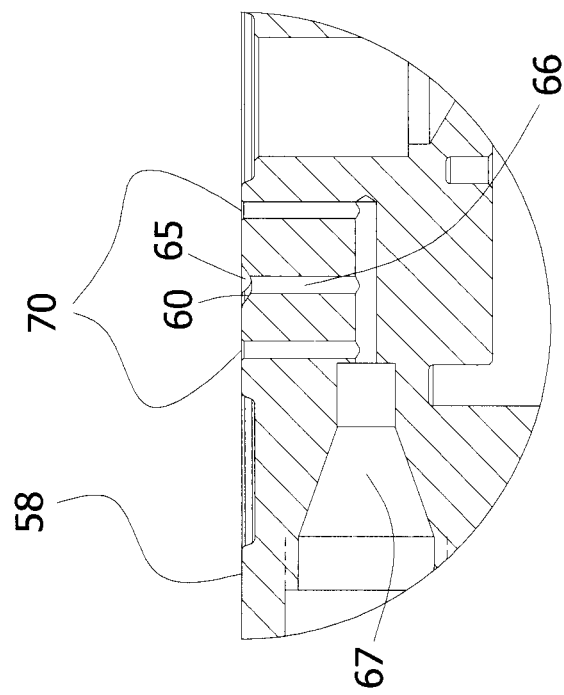
FIG. 8C is an enlarged view of section 8C of FIG. 8B.
Figure 8F:
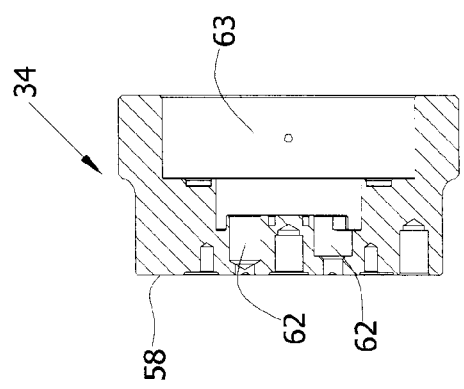
FIGS. 8F and 8G are cross-sectional side views of the valve body along line F-F and G-G of FIG. 8E, respectively.
Figure 8H:
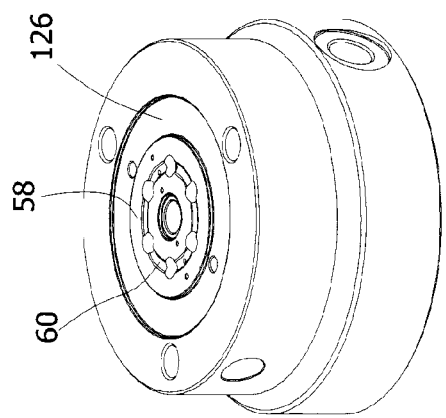
FIG. 8H is a top perspective view of the valve body of FIG. 8A.
Figure 8E:
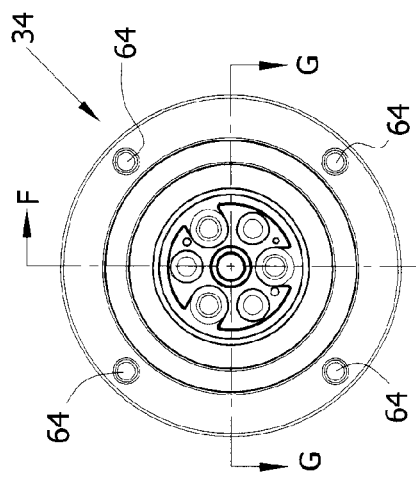
FIG. 8E is a bottom view of the valve body of FIG. 8A.
Figure 8G:
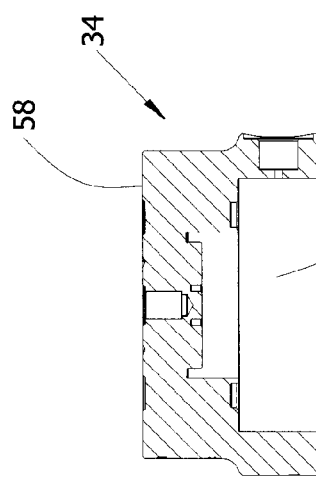

Still referring to FIGS. 2 and 4 to 6, and more clearly shown in FIGS. 7A to 7E, the valve cap 32 has an interface, hereinafter referred to as the first interface 42, and a plurality of process conduits 44 extending through it. This first interface 42 is flat and smooth, and is in contact with the diaphragm 36 when the valve is assembled (as shown in FIGS. 4 to 6). Each process conduit 44, in this preferred embodiment amounting to six (6), ends in a process port 46 opening at the first interface 42. The process ports 46 are preferably circularly arranged on the first interface 42. Best shown in FIG. 7C, each of the process conduits 44 are preferably formed by a larger threaded hole 48 for receiving tubing connections and a smaller fluid passage 50 ending in the process port 46. In this embodiment, the valve cap 32 has a cylindrical shape and is for example made of electro-polished stainless steel. The valve cap 32 is also provided with screw holes 52 for receiving socket head cap screws 54 (shown in FIG. 2), for holding the valve cap 32 to the cylinder 34. The alignment of the valve cap 32 with the cylinder 34 is ensured by dowel pins 56 (also shown in FIG. 2). Of course, other arrangements for holding the valve cap 32 to the cylinder 34 can be considered. Optionally, a layer of polymer covers the first interface 42 of the valve cap 32. Other materials, for example ceramic or various types of polymers, may be used as material for the valve cap 32. Shapes other than a cylindrical one may also be considered. Of course, other embodiments of the valve cap may include 4, 8, 10, 12 or any other convenient number of process ports.

Cylinder

Figure 2:
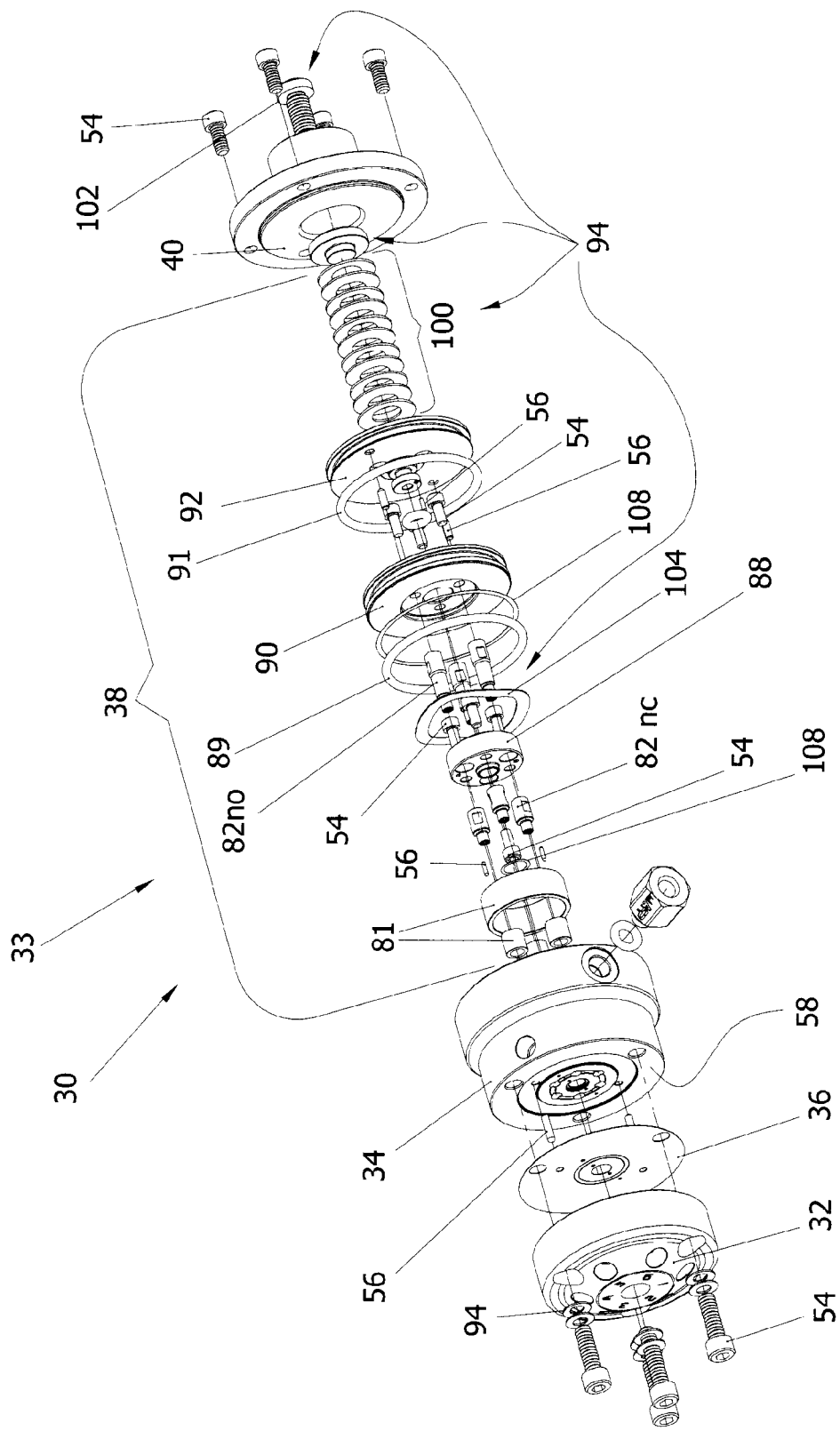
FIG. 2 is an exploded perspective view of a diaphragm-sealed valve in accordance with an embodiment of the invention.
Figure 3:
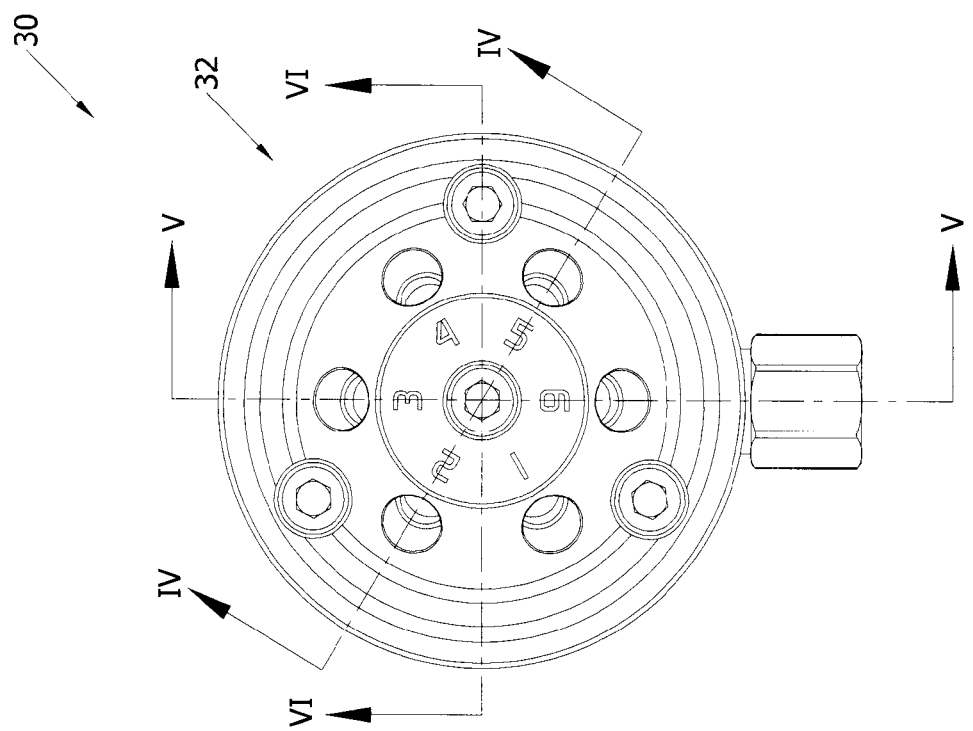
FIG. 3 is a top view of a diaphragm-sealed valve of FIG. 2.

Now referring to FIGS. 8A to 8G, there is shown a preferred embodiment of the cylinder 34 of the valve 30. Such as for the valve cap 32 described above, the cylinder 34 also has an interface, hereinafter referred to as the second interface 58, which faces the first interface 42 of the valve cap when the valve is assembled (as shown in FIGS. 4 to 6). Just as the first interface 42 of the valve cap 32, it is smooth and flat. The second interface 58 is provided with a main recess 60, preferably having a circular outline and it is aligned with the process ports 46 of the valve cap 32 when the valve elements are assembled and the valve is ready for use, as in FIGS. 4 to 6. The cylinder 34 also includes a plurality of plunger passages 62 (more clearly shown in FIG. 8F) each extending in the cylinder 34 and opening at one end in the main recess 60 between two of the process ports 46. The other ends of the plunger passages 62 open in a valve body cavity 63 which is for housing the plunger assembly 38 (as shown in FIG. 2). The valve body is also provided with a first set of screw holes 64 for receiving the socket head cap screws 54 that hold the valve body to the valve cap (best shown in FIG. 8A) and a second set of screw holes 64 for receiving the socket head cap screws 54 that hold the cylinder 34 to the bottom cap 40 (best shown in FIG. 8D). Of course, other arrangements could be considered for affixing the cylinder 34 to the bottom cap 40.

Diaphragm

Figure 9D:
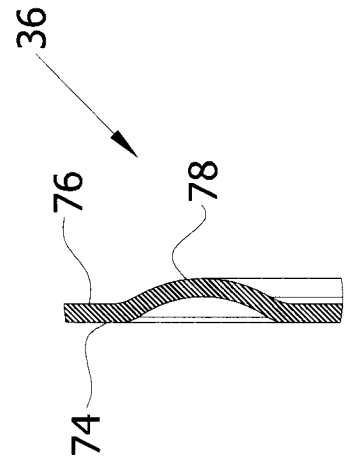
FIG. 9D is a perspective view of the diaphragm of FIG. 9A.
Figure 9C:
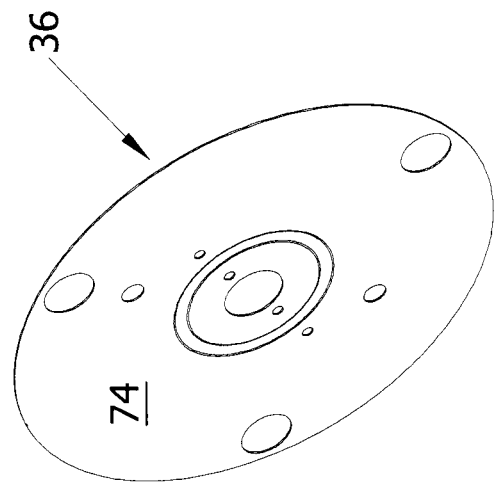
FIG. 9C is an enlarged view of section 9B of FIG. 9B.
Figure 9B:
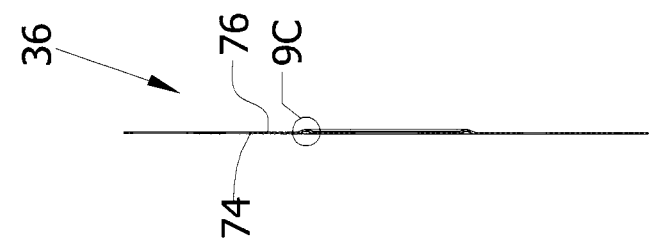
FIG. 9B is a cross-sectional side view of the diaphragm along line B-B of FIG. 9A.
Figure 9A:
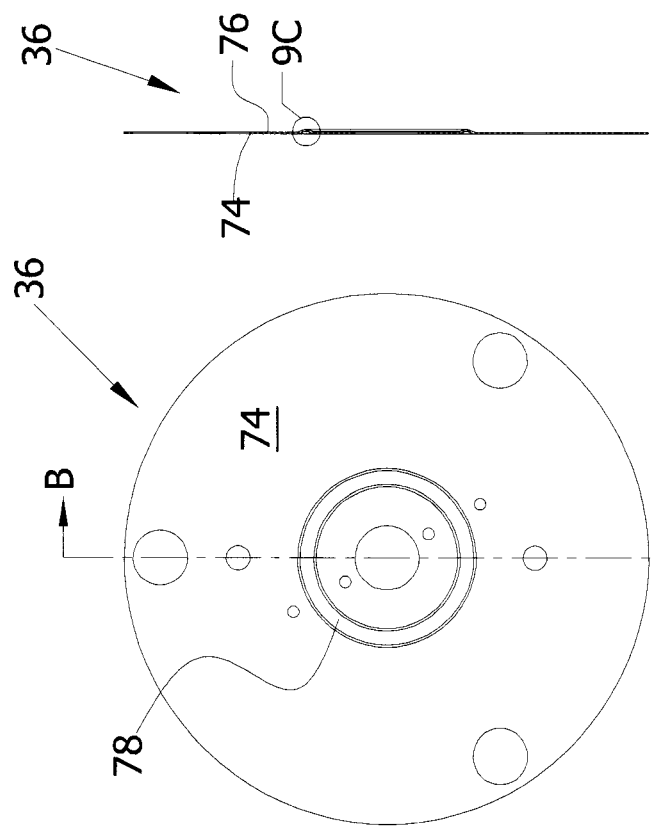
FIG. 9A is a top view of the diaphragm of the valve of FIG. 2, according to a preferred embodiment of the present invention.

Now referring to FIGS. 2, 4D and also to FIGS. 9A to 9C, there is shown a preferred embodiment of the diaphragm 36 of the valve 30. The diaphragm 36 has a first surface 74 facing the valve cap 32 and a second surface 76 facing the cylinder 34, the diaphragm 36 being compressibly positioned between the first 42 and the second 58 interfaces when the valve is assembled and ready for use (as in FIGS. 4 to 6). As more clearly shown in FIG. 4D, the diaphragm has a pre-formed deformation 78 lying within the main recess 60 of the cylinder 34, the first surface 74 of the diaphragm 36 defining with the first interface 42 of the valve cap 32 a communication channel 80 between the process ports.

The diaphragm 36 can be made of multiple layers of polymer, with or without a thin metallic layer, or alternatively be made of metal only. Metals that may be used are stainless steel 316, aluminium, chrome-nickel alloy, copper and the like. For applications requiring high gas-tightness sealing, a diaphragm 36 made of multiple layers of polymer is preferably used, while other applications require a thin metallic layer over the polymer layers.

Leaks Collection

With additional reference to FIG. 8B, the cylinder 34 may also be provided with a leak collection system comprising a process purging channel 65 extending along the main recess 60, a process purging inlet passage 66 and process purging outlet passage 68. The process purging inlet passage 66 is connected to an entry 67 of a purge line, and the process purging outlet passage 68 is connected to an exit 69 of a purge line. The cylinder 34 may further provided with a pair of fluid inlets 70 and a pair of fluid outlets 72, the pair of fluid inlets 70 also being connected to the entry 67 of a purge line, and the pair of fluid outlets 72 being connected the exit 69 of the purge line. The cylinder 34 may be provided with an actuation purging outlet passage 112. As seen in FIG. 7D, a purge circulation line may further be provided which includes inner and outer annular channels 51 and 53 extending at the first interface 42 of the valve cap 32. The fluid inlets 70 and the fluid outlets 72 each has a first opening 84 in the inner annular channel 51 and a second opening 86 in the outer annular channel 53.

The operation of such a preferred leak collection system is described in detail in the present Applicant's above-mentioned application PCT/CA2008/002138 and will not, as such, be described further herein.

Plunger Assembly

Referring to FIGS. 2 and 6, 6A and 6B, there is shown a preferred embodiment of a plunger assembly 38 of the valve 30. In this preferred embodiment, the plunger assembly 38 (as indicated in FIG. 2) has a plurality of plungers 82, each placed in one of the plunger passages 62 (more clearly shown in FIGS. 6A and 6B) of the cylinder 34. The term "plunger" is understood to mean a mechanism component driven by or against a mechanical force or fluid pressure. The plungers 82 can slide in the passages 62, between a closed position and an open position. In the closed position, the plunger 82 projects towards the first interface 42, and presses the diaphragm 36 against the first interface 42 of the valve cap 32, between two adjacent ports 46 for interrupting communication between these ports 46. In the open position, the plunger 82 is retracted within the cylinder 34 and extends away from the diaphragm 36 for allowing communication between the two adjacent ports 46. Preferably, each plunger 82 of the plunger assembly 38 is either a normally closed plunger $82nc$ or a normally open plunger $82no$. Still preferably, guide sleeves 81 surround the normally open plungers $82no$, for facilitating the movement of the plungers into the passages. The left side plunger of FIG. 6 is shown in the closed position, whereas the right side plunger is shown in the open position. Of course, plungers may take other shapes than that of a cylinder, as long as they can be in an open position where communication between the two adjacent ports 46 is allowed, and a closed position where communication between the two adjacent ports 46 is shut off. Other possible types of plungers 82 may include for example bearing balls.

As shown in FIGS. 2, 5 and 6, the plunger assembly further includes a first support structure 87 onto which the normally closed plungers $82nc$ are mounted, and a second support structure 89 onto which the normally open plungers $82no$ are mounted.

The valve 30 further comprises biasing means 94 for biasing the normally closed plungers $82nc$ towards the diaphragm 36 and the normally open plunger $82no$ away from the diaphragm 36. The valve body 33, the plunger assembly 38 and the locking mechanism 119 can be considered to form a valve body assembly.

An actuating mechanism 96 is further provided for actuating the valve 30, as will be described in further detail herein below.

The support structures 87 and 89 are used in displacing the plungers 82 within the passages 62. Preferably, the first support structure 87 comprises a push plate 88 and a first piston 92 and the second support structure 89 comprises a second piston 90. As illustrated, the first piston 92 is located below the second piston 90 and for simplicity these two pistons will hereinafter be referred to as the lower piston 92 and the upper piston 90, respectively. Alternatively, it is also sometimes convenient to refer to the first piston 92 as the normally closed piston 92 since it supports the normally closed plungers $82nc$. Similarly, the second piston 90 may also be referred to as the normally open piston 90 since it supports the normally open plungers $82no$.

Figure 11B:
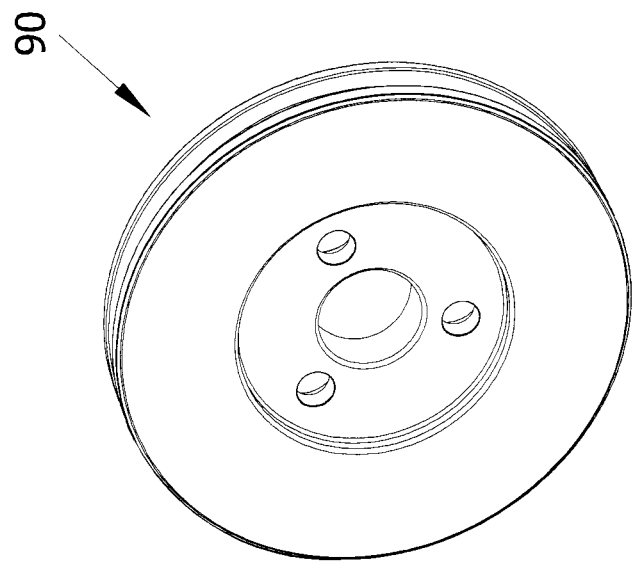
FIG. 11B is a top perspective view of the normally open piston of FIG. 2.
Figure 11A:
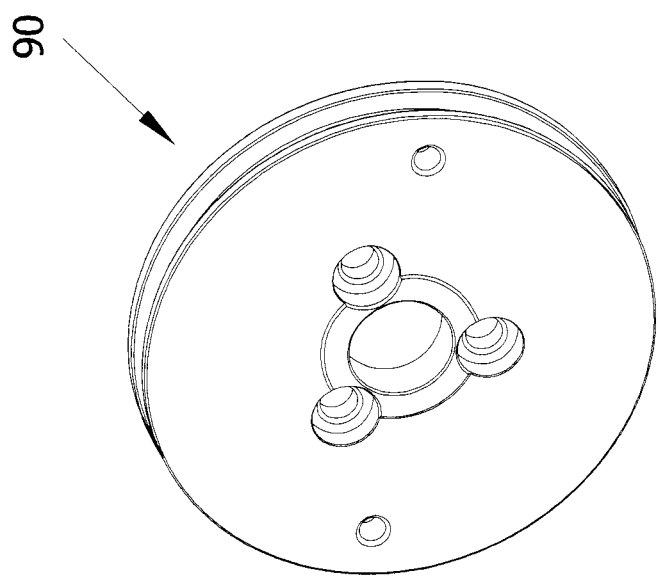
Figure 12B:
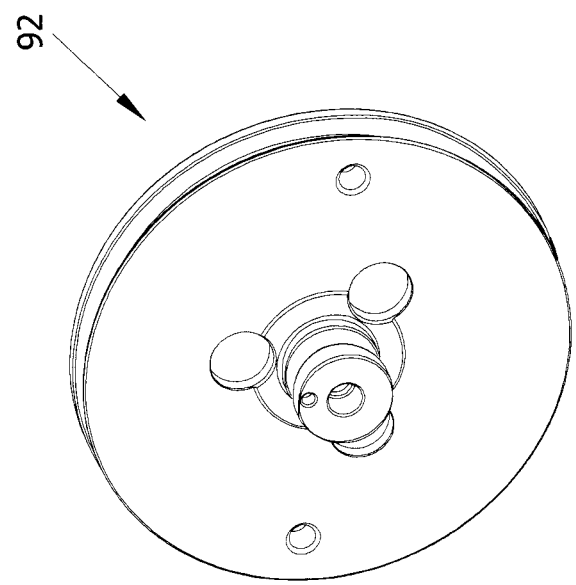
FIG. 12B is a top perspective view of the normally closed piston of FIG. 2.
Figure 12A:
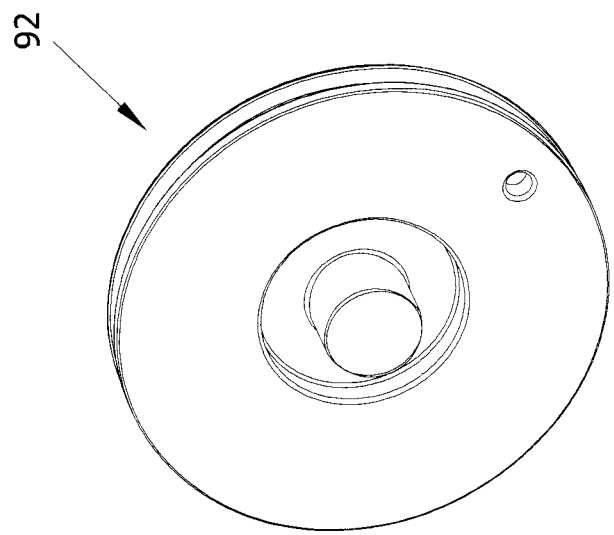
Figure 13B:
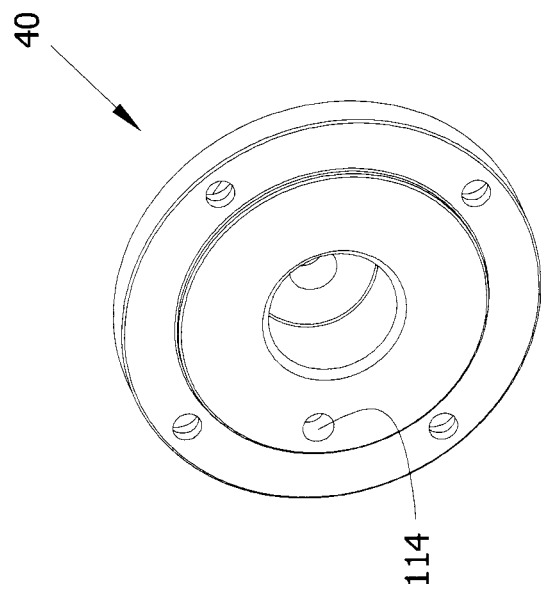
FIGS. 13A and 13B are a bottom perspective view and a top perspective view of the bottom cap of FIG. 2, respectively.
Figure 13A:
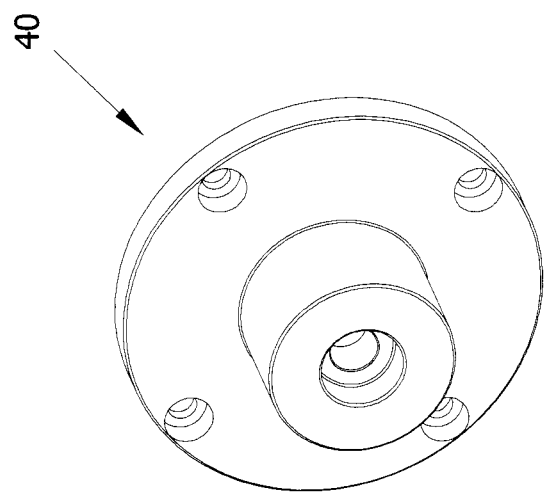

The push plate 88 extends within the cavity 63 of the cylinder 34, in parallel to the second interface 58 of the cylinder 34, i.e. perpendicular to the plunger passages 62 and the central axis of the cylinder 34. The push plate 88 is movable transversally to the second interface 58, or in other words in parallel to the central axis of the cylinder 34. The normally closed plungers $82nc$ are mounted on the push plate 88. A guide sleeve 81 surrounds the push plate 88 for facilitating its movement within the upper section of the cavity 63 of the cylinder 34. A plurality of cavities 98 (shown in FIGS. 10A to 10C) extend across the push plate 88 for allowing the normally open plungers $82no$ to pass through it. The upper piston 90 extends contiguously under the push plate, the normally opened plungers $82no$ being placed on it. The lower piston 92 extends under the upper piston 90 contiguously to it, the lower piston 92 being rigidly connected to the push plate 88, preferably with a screw 54. O-rings 91 are preferably provided on the outline of each pistons, to properly seal the upper 92 and lower 90 pistons to the inner surface of the cylinder 34. In this preferred embodiment, when either the upper 90 or lower pistons 92 are retracted, their corresponding plungers 82 attached thereto are pulled down, ensuring that it does not press against the diaphragm 36. Thus, with this particular design, the valve 30 can advantageously be mounted in any position, since there are no "floating" plungers. FIGS. 11A and 11B show more clearly the upper piston 90 of this preferred embodiment, while FIGS. 12A and 12B show more clearly the lower piston 92.

More clearly shown in FIGS. 2 and 4, biasing means 94 ensure that the lower piston 92 is upwardly biased and that the upper piston 90 is downwardly biased. Preferably, a Belleville washer 100 assembly cooperates with the lower piston 92 and a bottom cap screw 102 controls an upward force on the Belleville washer assembly 100. Still preferably, it is a disc spring 104 extending over the upper piston 90 that exerts a downward force on the upper piston 90 and therefore downwardly biases it.

Now referring to FIG. 5, to actuate the plungers, the actuating mechanism 96 controls a distance or space between the upper 90 and lower 92 pistons. In this preferred embodiment, it can be seen that the actuating mechanism 96 actuates the plungers 82 between the opened and closed positions, by injection of actuation gas between the upper 90 and lower 92 pistons, the actuating mechanism being pneumatic actuators.

Referring to FIGS. 2, 5, 5A and 5B, in order to avoid situations where an over pressurising of the actuator damages the diaphragm, the pistons 90, 92 are may advantageously be provided with some room therearound to add shims 108 of various thicknesses. These shims 108 stop the piston travelling, since the piston will seat thereon. The idea is to use the right shim thickness for a particular application. These shims 108 are advantageously used on the normally open piston 90 (or upper piston), more clearly shown in FIG. 5B, but also on the pushe plate 88 which is connected to the normally closed piston 92, more clearly shown in FIG. 5A. However, it is important to note that the use of such shims 108 on the normally closed piston 92 is not intended to avoid damage when using a higher operating pressure to actuate the valve 30, since pressure is used to lift the pistons to open the fluid communication channel between two adjacent ports 46.

In fact, if the bottom cap set screw 102 is particularly adjusted in order to require a high pressure to lift the corresponding piston 90, 92, the result is that the time that all ports 46 are closed upon valve actuation will advantageously be longer, then eliminating even more the risk of cross port flow or the so called "mixing". This higher pressure operation will not cause damages since the corresponding piston stroke is limited by the shims stack. This provides a convenient way to adjust or to "time" the valve sequence operation by setting the step of "all ports closed" more or less longer.

Now referring to FIGS. 2, 5, 13A and 13B, the bottom cap 40 is affixed to the cylinder 34, preferably with socket head cap screws 54, and it also houses the bottom cap set screw 102 that allow adjustment of the pressure exerted on the normally closed piston 92 via the Belleville washer assembly 100. The bottom cap 40 is also advantageously provided with a bottom cap actuation vent 114 extending in it and located opposite to the actuating mechanism 96 of the plunger assembly 38, for preventing pressure build up between the lower piston 92 and the bottom cap 40.

Locking Mechanism

The locking mechanism, which has been omitted from previous Figures for clarity, will now be described in detail in conjunction with FIGS. 14A to 21C. Oftentimes, after diaphragm valves are built and fully tested, they are sealed in plastic packages, packed and stored in inventory before shipping to customers. Depending on various factors such as market demand, inventory management, customer need and the like, valves are likely to stay unused for weeks or months after their manufacture. In addition, in some circumstances a valve owner may temporarily shut down or remove a valve from active use for an undetermined amount of time before putting it in service again. While a valve is idle, its normally closed plungers are in their closed position and therefore apply a constant pressure on the diaphragm. Depending on diaphragm material, this could lead to a permanent deformation of the diaphragm, and reduced efficiency of the valve. A pressure relief system is therefore advantageous provided to lock the normally closed in their open position when the valve is not in use.

A locking mechanism 119 in accordance with the present invention advantageously engages the first support structure 87 when the normally closed plungers 82nc are in an open position, thereby acting against the biasing means 94 and physically preventing those plungers 82nc from reaching a closed position. As will be appreciated by one of ordinary skill in the art, the use of such a locking mechanism 119 can advantageously be used to prevent the normally closed plungers 82nc from deforming, compressing or otherwise acting upon the diaphragm 36 when the valve 30 is not in use.

It will also be appreciated that such locking mechanism 119 can also advantageously ease replacement of the diaphragm during maintenance and the like. By enabling a user to restrain the normally closed plungers within the valve body, it can be assured that those plungers do not interfere with the proper positioning of the diaphragm.

FIGS. 14A to 15C illustrate a first embodiment of the locking mechanism 119. The cylinder 34 includes at least one transverse passage 122 extending therethrough from a side of the valve 30 to the lower piston 92. The lower piston 92 also includes such a transverse passage 124, which is aligned with the transverse passage 122 of the cylinder 34 when the lower piston 92 is lowered, and the normally closed plungers 82nc therefore is in the open position.

Figure 14A:
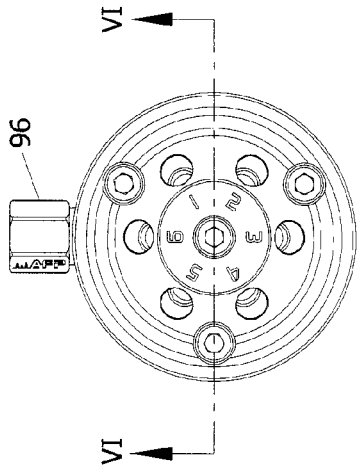
FIG. 14A is a top view of a diaphragm-sealed valve according to a first preferred embodiment of present invention.
Figure 14C:
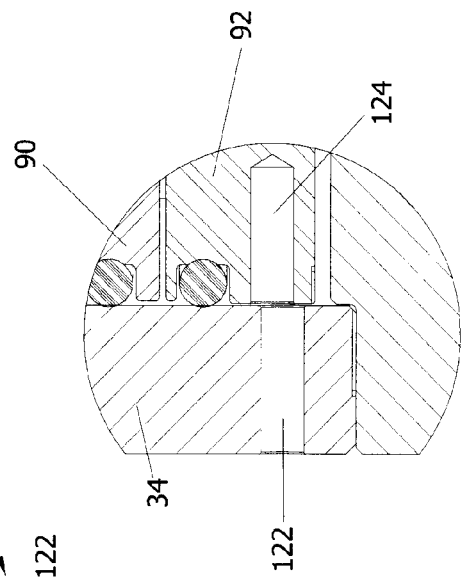
FIG. 14C is an enlarged view of section 14C of FIG. 14B.
Figure 14B:
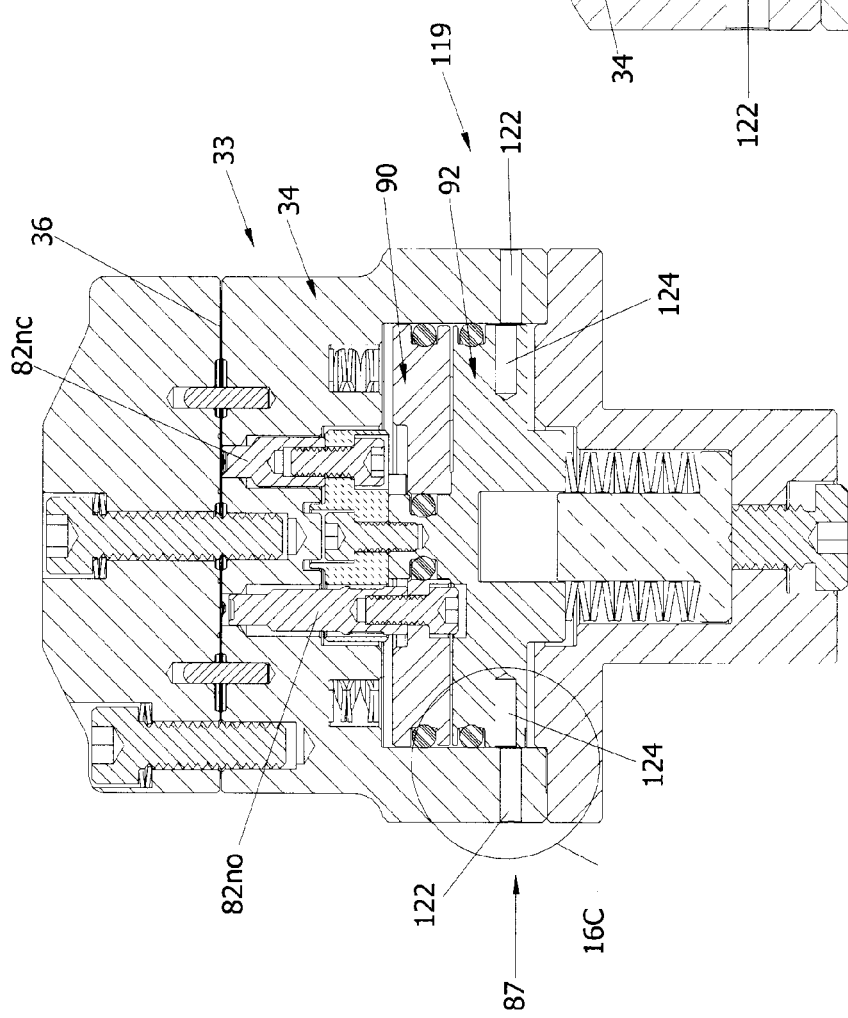
FIG. 14B is a cross-sectional side view of the diaphragm-sealed valve of FIG. 14A taken along line VI-VI.
Figure 15A:
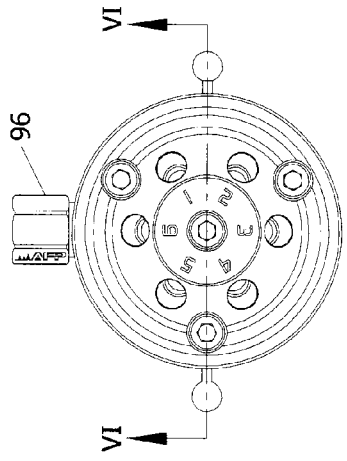
FIG. 15A is a top view of the diaphragm-sealed valve of FIG. 14A, with locking pins inserted.
Figure 15C:
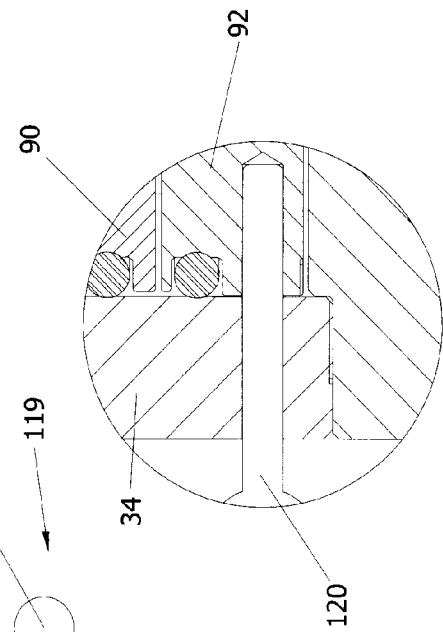
FIG. 15C is an enlarged view of section 15C of FIG. 15B.
Figure 15B:
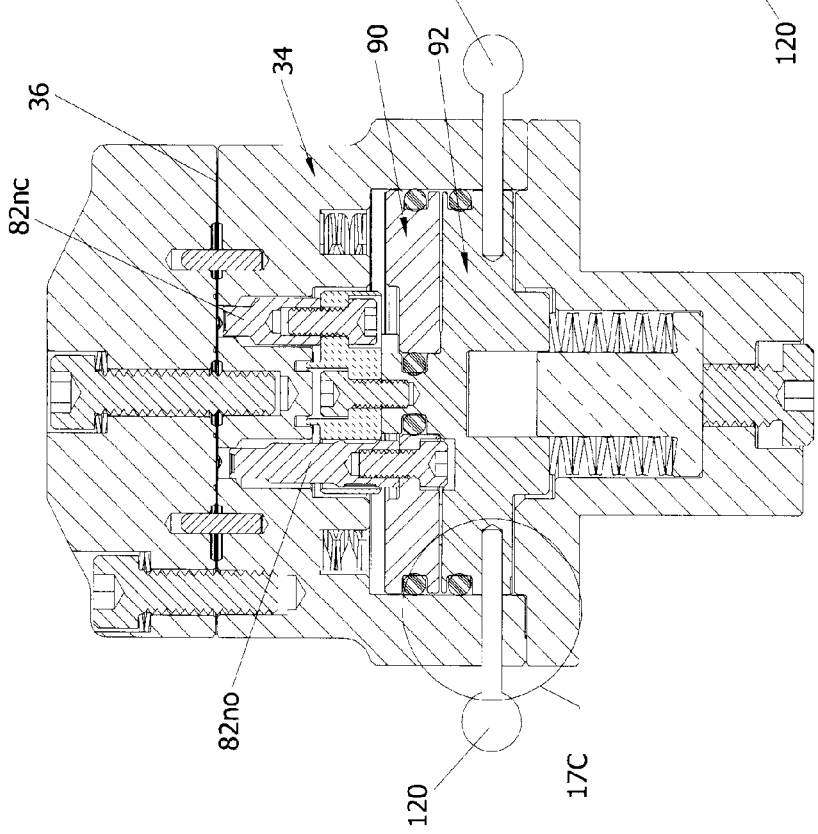
FIG. 15B is a cross-sectional side view of the diaphragm-sealed valve of FIG. 15A take along line VI-VI.

In FIGS. 14A to 14C, the normally closed plungers 82nc are in the closed position and the transverse passages 122 and 124 do not align. In FIGS. 15A to 15C however, the normally closed plungers 82nc, as well as the first support structure 87, have been retracted away from the diaphragm. A locking pin 120 then insertable through the aligned transverse passages 122 and 124 of the cylinder 34 and lower piston 92.

In order to lock the valve, the actuating mechanism 96 is preferably activated: the lower piston 92 is forced downward by supplying pressurized gas between the upper and lower pistons 90 and 92 as explained above. This brings the transverse passages 122 and 124 of the cylinder 34 and lower piston 92 into alignment, and the locking pin 120 can be inserted therein. Once the locking pin 120 is in place, the actuating mechanism 96 can be deactivated, and both the normally closed 82nc and to normally opened 82no plungers will remain in their open position, leaving the diaphragm 36 free of mechanical stress thereon. The valve 30 can simply be reactivated and the locking pin 120 removed whenever the valve 30 needs to be used again. It will be appreciated that various other means for retracting the lower piston 92 and the normally closed plungers 82nc may similarly be used.

With reference to FIGS. 16A to 16C, a second preferred embodiment of the locking mechanism 119 is illustrated. This second embodiment is similar to that illustrated in FIGS. 14A to 15C in that it provides at least one pin 121 which is adapted to be inserted first through a first transverse passage 122 in the valve body 33 and then though a second transverse passage 124 in the first support structure 87. Also like in FIGS. 14A to 15C, the first transverse passage 122 is provided through the cylinder 34 and the second transverse passage 124 is provided through the lower piston 92.

The embodiment of FIGS. 16A to 16C differs from that of FIGS. 14A to 15C in that the locking pin 121 is provided with a flat extremity 130 having a first thickness 132 and a second thickness 134, the latter being greater than the former. The second transverse passage 124 is provided with a corresponding shape. The pin 121 is rotatable within the passages 122 and 124 between a first orientation (seen in FIG. 16A) and a second orientation (seen in FIG. 16B). In the first orientation, it is the smaller, first thickness 132 which is oriented vertically, i.e. in line with the plunger passages. Despite the presence of the pin 121 in both passages 122 and 124, the lower piston 92 remains free to travel between the open and closed positions as the first thickness 132 does not fill the second passage 124. In the second orientation however, the pin 121 has been rotated 90° such that the second thickness 134 is oriented vertically. In this orientation, the larger second thickness 134 fills the second passage 124 vertically, thereby preventing the first piston from moving with respect to the cylinder 34 and blocking the normally closed plungers 82nc the open position.

By rotating the pin 121 from the first orientation to the second, it operates as a cam, pushing the second piston 92 downwards. In this manner, this second embodiment not only allows the user to manually restrain the normally closed plungers 82nc in the open position, but also avoids the need to remove the pins 121 during use. It will be appreciated however that given a biasing means of sufficient strength, it could be inconvenient to manually actuate the locking mechanism 119. In such cases, the above-described method of activating the valve 30 with the actuating mechanism 96 can similarly be used.

Preferably, and as illustrated in both the embodiments of FIGS. 14A to 15C and 16A to 16C, two sets of transverse passages 122 and 124 and corresponding locking pins 120, 121 are provided at opposite positions around the valve body 33. It will be understood however that any number of passages 122 and 124 and pins 120 may be provided. Moreover, various other shapes or types of passages 122 and 124 and pins 120, 121 could similarly be used. In addition, it will be appreciated that the alignable passages 122 and 124 could be provided between other parts of the first support structure 87 and the valve body 33.

With reference to FIGS. 17A to 18E, third and fourth preferred embodiments of the locking mechanism 119 are illustrated. In both of these embodiments, the locking mechanism 119 comprises the combination of at least one restraining mechanism 140 and at least one extension 142. The extension 142 is mounted to the first support structure 87 and is movable therewith. The extension 142 extends through the valve body 33. The restraining mechanism 140 is positionable between both the body 33 and the extension 142 when the normally closed plungers 82nc are in the open position. In so doing, the restraining mechanism 140 engages both the valve body 33 and the extension 142 in order to prevent the latter from moving with respect to the former.

Figure 17B:
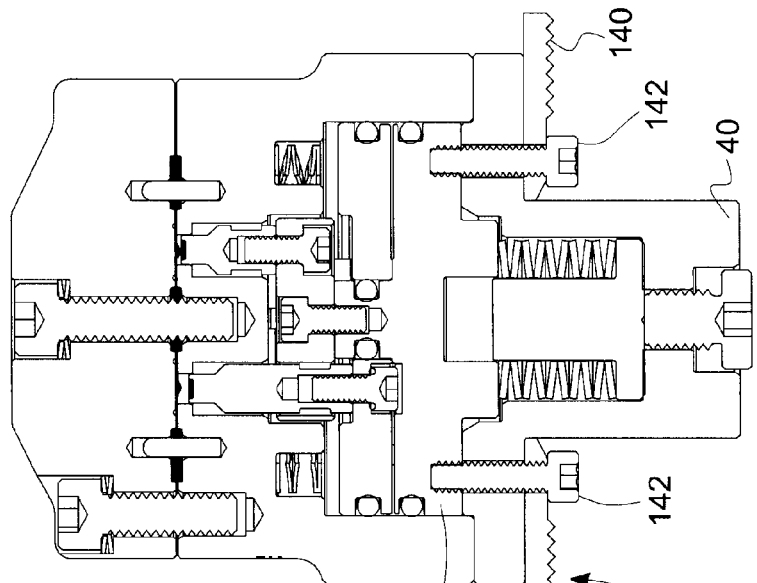
FIGS. 17A and 17B are cross-sectional views of a diaphragm-sealed valve according to a third preferred embodiment of the present invention.
Figure 17C:
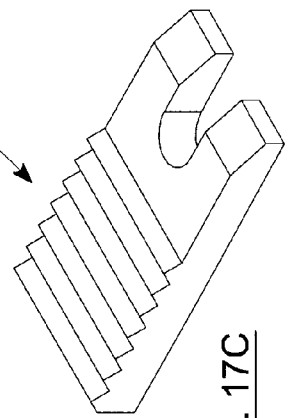
FIG. 17C is a perspective view of a lock clip in accordance with the embodiment of FIGS. 17A and 17B.
Figure 17A:
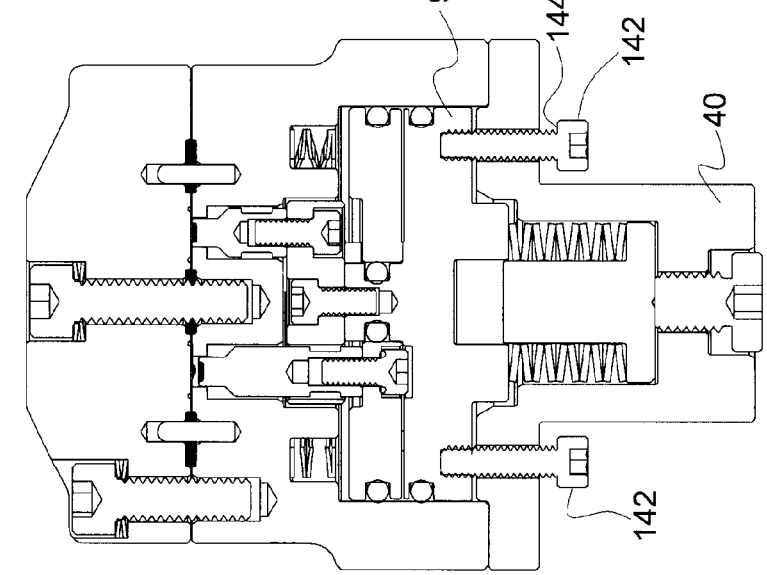

With specific reference to the third embodiment illustrated in FIGS. 17A to 17C, the extensions 142 extend downward from the lower piston 92, through the bottom cap 40. At the exposed end of the extension 142 is a shoulder 144 which faces the valve 30. In the illustrated embodiment, the extensions 142 are bolts and the shoulder 144 is the under-surface of the bolt head. In this embodiment, the restraining mechanism 140 is a locking clip which is able to be positioned between the shoulder 144 and the bottom cap 40 when the normally closed plungers 82nc are in the open position, as seen in FIG. 17B. It will be appreciated that the locking clip 140 could similarly be provided as pin which engages a corresponding hole through the end of the extension 142. Indeed, it will be similarly appreciated that such an extension/locking clip combination could similarly be provided between other elements of the valve body 33 and the first support structure 87.

With specific reference to the fourth embodiment illustrate in FIGS. 18A to 18E, the extensions 142 extend outwards from the lower piston 92, through holes 146 in the sides of the cylinder 34. Preferably, the hole 146 is provided with an elongated cross-section, as illustrated, so as to accommodate for the vertical travel of the extension 142. The restraining mechanism 140 is embodied herein as a hook which is attached to the base 40 and pivots about an axis 147 which is parallel to the extension 142. When the valve 30 is in use, the hook 140 may be pivoted away from its respective extension 142. When the normally closed plungers 82nc are in the open position, i.e. when the lower piston 92 is at its lowermost, the hook 140 may be pivoted such that it engages and restrains the extension 142.

Preferably, there are two sets of extensions 142 and hooks 140 provided at opposition positions around the valve 30, although it will be appreciated that more or less extensions 142 and hooks 140 could similarly be used. It will also be appreciated that the extension 142 could similarly extend from and through different parts of the first support structure 87 and the valve body 33, respectively, and the hook 140 could be mounted at a different part of the valve body 33.

With reference to FIGS. 19A to 21C, the fifth, sixth and seventh embodiments of the locking mechanism 119 are illustrated. In each of these three embodiments, the locking mechanism 119 comprises a threaded passage 150 which extends downwards through the valve body 33, and a locking screw 152 which can be positioned at a locking position which engages and blocks the first support structure 87 and the normally closed plungers 82nc in the open position.

Figure 19B:
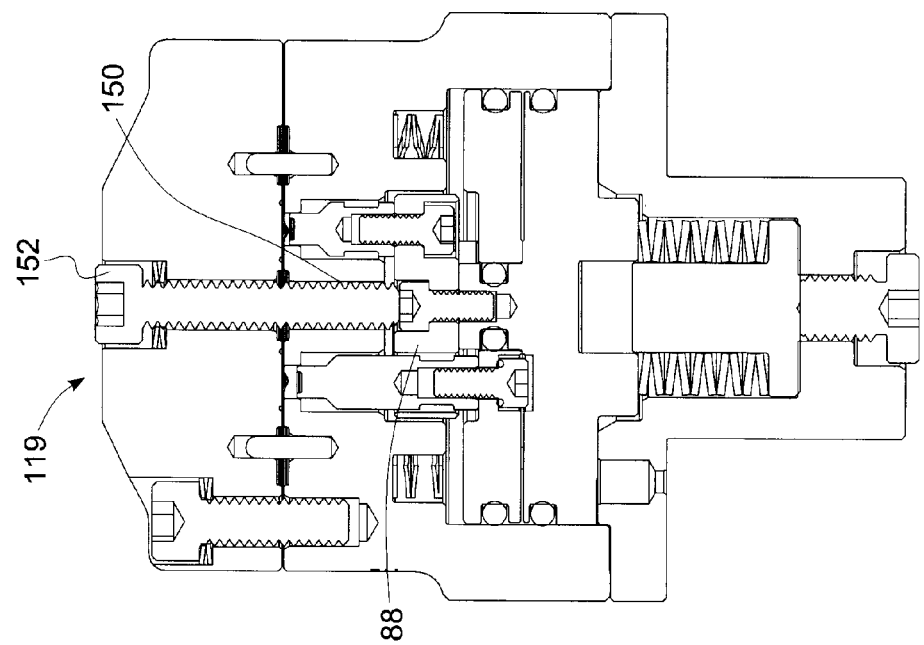
Figure 19A:
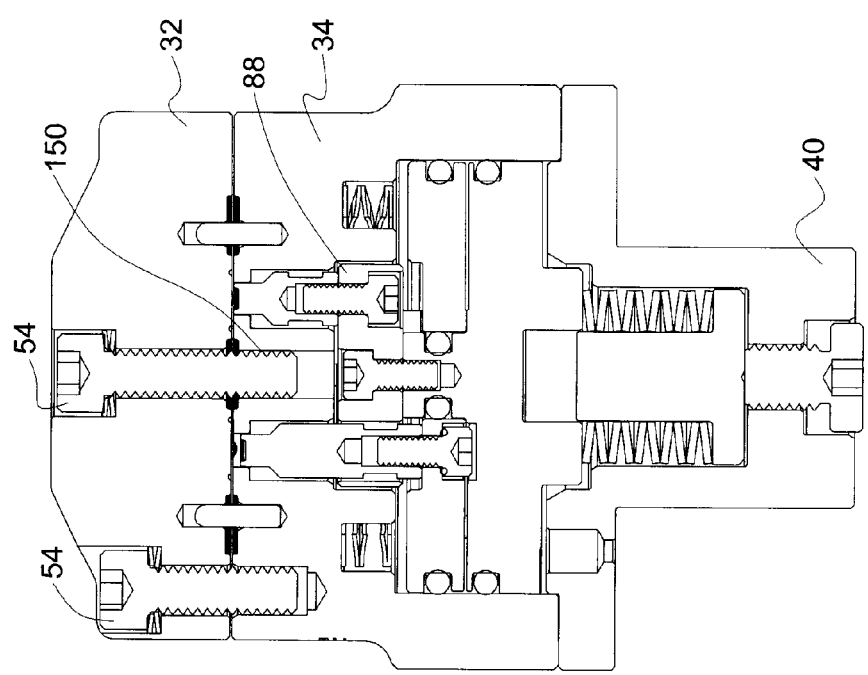

With specific reference to FIGS. 19A and 19B, one of the cap screws 54 which fix the valve cap 32 to the cylinder 34, preferably the central one, is replaced with the longer locking screw 152 which is able reach a locking position where it is engages the top of the push plate 88 when the latter is in open position. When the locking screw 152 is at the locking position, as seen in FIG. 19B, the normally closed plungers 82nc are kept in the open position. Alternatively, a single locking 152 screw may be provided in place of a regularly sized cap screw and lowered with respect to the plunger assembly 38 to the locking position accordingly.

With specific reference to FIGS. 20A to 20D, the central cap screw 54 is provided with an internally threaded passage 150 which is able to receive a smaller diameter locking screw 152. In order to restrain the normally closed valves 82nc in the open position, the locking screw 152 is lowered to the locking position shown in FIGS. 20B and 20D wherein it engages the push plate 88 and thereby prevents the normally closed plungers 82nc from returning to the closed position.

With specific reference to FIGS. 21A to 21C, the central cap screw 54 is provided with a cap screw passage 156, which is unthreaded, through which the locking screw 152 is able to pass. The threaded passage 150 is provided within the push plate 88 (rather than through the cap screw 54 itself), aligned below the unthreaded cap screw passage 156. Once again, the locking screw 152 may be lowered to the locking position shown in FIGS. 21B and 21C in order to restrain the push plate 88 and the normally closed plungers 82nc in the open position.

It will be appreciated by one of ordinary skill in the art that the above mentioned advantages of a locking mechanism in accordance with the present invention could similarly be used with many other types of diaphragm-sealed valves, especially those including normally-closed valves.

Although preferred embodiments of the present invention have been described in detail herein and illustrated in the accompanying drawings, it is to be understood that the invention is not limited to these precise embodiments and that various changes and modifications may be effected therein without departing from the scope of the present invention.

The invention claimed is:

1. A valve comprising:
    a valve cap comprising a plurality of process conduits extending therethrough, each of the process conduits ending in a process port;
    a valve body facing the valve cap, the valve body comprising a plurality of plunger passages extending therein;
    a diaphragm positioned across the process ports and between the valve cap and the valve body;
    a plunger assembly comprising:
        a plurality of plungers, each of the plungers being positioned in a respective one of the plunger passages and slideable therein between a closed position wherein the plunger deforms the diaphragm in order to block communication between two of the process ports and an open position wherein the plunger is retracted away from the diaphragm, each of the plungers being either a normally closed plunger or a normally open plunger;
        a first support structure upon which the normally closed plungers are mounted; and
        a second support structure upon which the normally open plungers are mounted;
    a biasing mechanism for biasing the normally closed plungers towards the diaphragm and biasing the normally open plungers away from the diaphragm; and
    a locking mechanism for engaging the first support structure and thereby physically restrain the normally closed plungers in the open position.

2. A valve according to claim 1, wherein the locking mechanism comprises:
    a first transverse passage in the valve body which extends perpendicular to the plunger passages,
    a second transverse passage extending through the first support structure which is alignable with the first transverse passage when the normally closed plungers are in the open position; and
    a locking pin insertable through both the first and second transverse passages, thereby restraining the normally closed plungers in the open position.

3. A valve according to claim 2, wherein the locking pin comprises a flat extremity having first and second thicknesses, the first thickness being less than the second thickness, the locking pin rotatable within the first and second transverse passages between a first orientation wherein the first thickness is aligned with the plunger passages and a second orientation wherein the second thickness is aligned with the plunger passages.

4. A valve according to claim 1, wherein the locking mechanism comprises:
an extension mounted to the first support structure and which extends through the valve body, the extension being movable with the first support structure as the normally closed plungers slide between the open and closed positions; and
a restraining mechanism positionable between the valve body and the extension when the normally closed plungers are in the open position.

5. A valve according to claim 4, wherein the extension extends parallel to the plunger and ends with a shoulder, and wherein the restraining mechanism is a lock clip adapted to be inserted between the shoulder and the valve body when the normally closed plungers are in the open position.

6. A valve according to claim 4, wherein the extension extends perpendicular to the plunger passages, and wherein the restraining mechanism is a hook which is pivotable about the valve body and adapted to restrain the extension when the normally closed plungers are in the open position.

7. A valve according to claim 1, wherein the locking mechanism comprises:
a threaded passage extending through the valve body parallel to the plunger passages; and
a locking screw adapted to threadedly engage the threaded passage and be positioned at a locking position wherein the locking screw engages the first support structure thereby restraining the normally closed plungers in the open position.

8. A valve according to claim 7, wherein the valve body comprises a plurality of cap screws for fixing the valve cap thereto, the locking screw being one of the plurality of cap screws.

9. A valve according to claim 7, wherein the valve body comprises a plurality of cap screws for fixing the valve cap thereto, the threaded passage extending through one of the plurality of cap screws.

10. A valve according to claim 7, wherein the valve body comprises a plurality of cap screws for fixing the valve cap thereto, one of the plurality of cap screws being provided with a cap screw passage aligned with the threaded passage, the locking screw being adapted to pass through the cap screw passage in order to engage the threaded passage.

11. A valve according to claim 1, wherein the first support structure comprises a push plate extending within the valve body and movable therewithin, the normally closed plunger being mounted on the push plate.

12. A valve according to claim 11, wherein the first support structure further comprises a first piston extending within the valve body parallel to the push plate and connected rigidly thereto, the locking mechanism engaging one of the push plate and the first piston.

13. A valve according to claim 12, wherein the second support structure comprises a second piston extending within the valve body and movable therewithin between the push plate and the first piston, the normally open plungers being mounted on the second piston; the push plate comprising a plurality of cavities extending thereacross for allowing passage of the normally open plungers.

14. A valve according to claim 13, further comprising an actuating mechanism for actuating the normally closed and normally open plungers between the opened and closed positions thereof, the actuating mechanism controlling a distance between the first and second pistons.

15. A valve according to claim 1, wherein the valve body comprises a cylinder in which the first and second support structures are translatable and a bottom cap affixed to the cylinder opposite the valve cap.

16. A valve body assembly for a valve comprising a valve cap, the valve cap comprising a plurality of process conduits extending therethrough, each of the process conduits ending in a process port, the valve further comprising a diaphragm positioned across the process ports, the valve body assembly comprising:
a valve body comprising a plurality of plunger passages extending therein, the diaphragm being positioned between the valve body and the valve cap;
a plunger assembly comprising:
a plurality of plungers, each of the plungers being positioned in a respective one of the plunger passages and slideable therein between a closed position wherein the plunger is adapted to deform the diaphragm in order to block communication between two of the process ports, and an open position wherein the plunger is retracted away from the diaphragm, each of the plungers being either a normally closed plunger or a normally open plunger;
a first support structure upon which the normally closed plungers are mounted; and
a second support structure upon which the normally open plungers are mounted;
a biasing mechanism for biasing the normally closed plungers towards the diaphragm and biasing the normally open plungers away from the diaphragm; and
a locking mechanism for engaging the first support structure and thereby physically restrain the normally closed plungers in the open position.

17. A valve body assembly according to claim 16, wherein the locking mechanism comprises:
a first transverse passage in the valve body which extends perpendicular to the plunger passages,
a second transverse passage extending through the first support structure which is alignable with the first transverse passage when the normally closed plungers are in the open position; and
a locking pin insertable through both the first and second transverse passages, thereby restraining the normally closed plungers in the open position.

18. A valve body assembly according to claim 16, wherein the locking mechanism comprises:
an extension mounted to the first support structure and which extends through the valve body, the extension being movable with the first support structure as the normally closed plungers slide between the open and closed positions; and
a restraining mechanism positionable between the valve body and the extension when the normally closed plungers are in the open position.

19. A valve body assembly according to claim 16, wherein the locking mechanism comprises:
a threaded passage extending through the valve body parallel to the plunger passages; and
a locking screw adapted to threadedly engage the threaded passage and be positioned at a locking position wherein the locking screw engages the first support structure thereby restraining the normally closed plungers in the open position.

* * * * *